(12) United States Patent
Kim et al.

(10) Patent No.: US 8,841,432 B2
(45) Date of Patent: Sep. 23, 2014

(54) SHUTTLE VECTORS FOR MYCOBACTERIA-ESCHERICHIA COLI AND USES THEREOF

(75) Inventors: Bum-Joon Kim, Seoul (KR); Hyungki Lee, Suwon-si (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/450,689

(22) Filed: Apr. 19, 2012

(65) Prior Publication Data
US 2012/0270322 A1   Oct. 25, 2012

(30) Foreign Application Priority Data
Apr. 21, 2011  (KR) .................. 10-2011-0037147

(51) Int. Cl.
| | | |
|---|---|---|
| C07H 21/04 | (2006.01) | |
| C12N 15/00 | (2006.01) | |
| C12N 1/00 | (2006.01) | |
| A61K 39/04 | (2006.01) | |
| C12N 15/11 | (2006.01) | |

(52) U.S. Cl.
USPC ..... 536/23.1; 536/23.2; 536/23.5; 536/23.51; 536/23.7; 536/24.1; 536/24.5; 536/23.72; 435/320.1; 435/253.1; 424/248.1; 514/44 R; 514/44 A

(58) Field of Classification Search
None
See application file for complete search history.

(56) References Cited

U.S. PATENT DOCUMENTS

2003/0170211 A1*  9/2003  Goudsmit et al. ............ 424/93.2
2008/0268541 A1* 10/2008  Jacobs et al. .................. 435/455

FOREIGN PATENT DOCUMENTS

| EP | 0 329 822 | 6/1994 |
|---|---|---|
| EP | 0 439 182 | 4/1996 |
| WO | WO 88/10315 | 12/1988 |
| WO | WO 89/06700 | 7/1989 |
| WO | WO 90/01069 | 2/1990 |
| WO | WO 90/06995 | 6/1990 |
| WO | WO 99/07409 | 2/1999 |
| WO | WO 99/32619 | 7/1999 |
| WO | WO 00/44895 | 8/2000 |
| WO | WO 00/44914 | 8/2000 |
| WO | WO 01/29058 | 4/2001 |
| WO | WO 01/36646 | 5/2001 |

OTHER PUBLICATIONS

Pashley et al (Applied and Environmental Microbiology, Jan. 2003, p. 517-523 vol. 69, No. 1).*
Stolt et al (Nucleic Acids Research, 1997, vol. 25, No. 19: 3840-3846).*
C. Yanofsky et al., "Repression Is Relieved Before Attenuation in the trp Operon of *Escherichia coli* as Tryptophan Starvation Becomes Increasingly Severe", Journal of Bacteriology, Jun. 1984, p. 1018-1024.
I. Herskowitz et al., "The Lysis-Lysogeny Decision of Phage λ: Explicit Programming and Responsiveness", Ann. Rev. Genet. 1980, 14:399-445.
J. R. de Wet et al., "Firefly Luciferase Gene: Structure and Expression in Mammalian Cells", Molecular and Cellular Biology, Feb. 1987, p. 725-737.
R. F. Selden et al., "Human Growth Hormone as a Reporter Gene in Regulation Studies Employing Transient Gene Expression", Molecular and Cellular Biology, Sep. 1986, p. 3173-3179.
M. Chalfie et al., "Green Fluorescent Protein as a Marker for Gene Expression", Science, New Series, vol. 263, No. 5148, (Feb. 11, 1994), pp. 802-805.
D. Hanahan, "Studies on Transformation of *Escherichia coli* with Plasmids", J. Mol. Biol. (1983) 166, 557-580.
W. J. Dower, et al., "High efficiency transformation of *E.coli* by high voltage electroporation", Nucleic Acids Research, vol. 16, No. 13, 1988, pp. 6127-6145.
M. C. Siomi et al., "PIWI-interacting small RNAs: the vanguard of genome defence", Nature Reviews, Molecular Cell Biology, vol. 12, Apr. 2011, pp. 246-258.
Xinzheng V. Guo et al., "Silencing Essential Protein Secretion in *Mycobacterium smegmatis* by Using Tetracycline Repressors", Journal of Bacteriology, Jul. 2007, pp. 4614-4623.

* cited by examiner

*Primary Examiner* — Richard Schnizer
(74) *Attorney, Agent, or Firm* — Stein IP, LLC

(57) ABSTRACT

The present disclosure provides a DNA molecule capable of replication in *Mycobacteria* having a nucleic acid sequence as disclosed in SEQ ID NO: 1, a shuttle vector constructed using it and a transformed cells containing the present vector. The vector of about 18 kb of the present disclosure contains 16 ORFs, a replication origin and a rep-like protein essential for replication. Therefore, the plasmid of the present disclosure can be utilized as a gene delivery system/research, and also in a therapeutic system such as immune therapeutics by effectively delivering proteins or heterologous DNA and expressing the encoded DNA in cells.

19 Claims, 15 Drawing Sheets

SHUTTLE VECTORS FOR MYCOBACTERIA-ESCHERICHIA COLI AND USES THEREOF

CROSS-REFERENCE TO RELATED APPLICATIONS

This application claims the benefit of Korean Application No. 10-2011-0037147, filed Apr. 21, 2011, in the Korean Intellectual Property Office, the disclosure of which is incorporated herein by reference.

BACKGROUND OF THE INVENTION

1. Field of the Invention

The present disclosure relates to shuttle vectors for *Mycobacteria* and *Escherichia coli* and their use.

2. Description of the Related Art

For the expression of heterologous proteins in eukaryotic cells, the transgene is usually introduced through a process called bactofection using viruses or bacteria as delivery systems. Consequently bacteria harboring protein encoding plasmids enter a eukaryotic cell and release the plasmid for uptake into the nucleus, where the plasmid encoded genes are expressed endogenously, and the plasmid may be either stably integrated into the genome of the cell or be present in the cytoplasm without being integrated into the genome. Particularly, *Mycobacteria* can be used advantageously as a delivery system for inducing/enhancing an immune response to proteins encoded in the plasmid because of its ability of disrupting immune tolerance in host at the cytotoxic T-level. At present, pAL5000 replicon is the most widely used vector as a *Mycobacteria-Escherichia coli* shuttle plasmid for a variety of uses. However the system has some drawbacks that the protein expressed from the vector in mycobacteria is not correctly folded and modified. Therefore there are demands for the new vector system which can correctly and reliably produce the encoded proteins.

SUMMARY OF THE INVENTION

The present disclosure provides a replicable DNA molecule derived from *Mycobacteria* having a nucleic acid sequence as disclosed in SEQ ID NO: 1.

In one aspect, the present disclosure provides a *Mycobacteria-Escherichia coli* shuttle vector comprising: (a) an origin of replication having a nucleic acid sequence as disclosed in SEQ ID NO: 2 (oriM); (b) an origin of replication for prokaryotic cells; (c) a promoter; and (d) a nucleic acid sequence encoding a target material, which is operatively linked to the promoter.

In another aspect, the oriM in the shuttle vector according to the present disclosure contains A+T rich region and direct repeat region.

In still other aspect, the promoter which may be used for the present disclosure includes a heat shock protein promoter, a CMV promoter, a promoter for 65 kDa common antigen of mycobacteria, ribosome RNA promoter from *Mycobacteria*, a promoter for MPB70, MPB59 or MPB64 antigen from *Mycobacterium bovis*, P1 promoter from bacteriophage Lamda, tac promoter, trp promoter, lac promoter, lacUV5 promoter, lpp promoter, PLλ promoter, PRλ promoter, rac5 promoter, amp promoter, recA promoter, SP6 promoter, T7 promoter, a promoter for kanamycin resistance gene of transposon Tn903 or Tn5, a promoter for metallothionine, a promoter for growth hormone or a hybrid promoter between eukaryotic and prokaryotic promoter, or a combination thereof.

In still other aspect, there is provided a shuttle vector which may encode a protein, antisense oligonucleotide, siRNA, shRNA, miRNA or piRNA.

In still other aspect, there is provided a shuttle vector which encoded a reporter protein, which includes, for example, a fluorescent protein, a beta-galactosidase, a chloramphenicol acetyl transferase, a human growth hormone, a urease or an alkaline phosphatase.

In still other aspect, there is provided a shuttle vector which encoded a fluorescent protein which includes, for example, GFP (green fluorescent protein), RFP (red fluorescent protein), CFP (cyan fluorescent protein), YFP (yellow fluorescent protein), BFP (blue fluorescent protein) or its variants.

In still other aspect, there is provided a shuttle vector which further includes one or more selective markers. The selective markers include for example genes conferring resistance to antibiotics which include kanamycin, hygromycin, ampicillin, streptomycin, penicillin, chloramphenicol, gentamicin, carbenicillin, geneticin, neomycin or tetracycline.

In still other aspect, there is provided a shuttle vector, wherein the origin of replication is provided in a separate expression vector as a co-transformation.

Also the present disclosure relates to a cell transformed with a vector as disclosed in the present disclosure.

In one aspect, the transformed cells in the present disclosure are derived from cells which include *Mycobacteria* or *Escherichia coli*.

In other aspect, the *Mycobacteria* includes *M. smegmatis*, *M. bovis*-BCG, *M. avium*, *M. phlei*, *M. fortuitum*, *M. lufu*, *M. partuberculosis*, *M. habana*, *M. scrofulaceum*, or *M. intracellulare*.

In other aspect, there is further provided a method of using a first and a second vector for expression of heterologous transgenes in a eukaryotic cell, wherein the first vector is the vector according to claim 1 or 2 and the second vector is pSE100 in eukaryotic cells.

In still other aspect, the transgenes encoded in the vector of the present method include a protein, antisense oligonucleotide, siRNA, ashRNA, miRNA or piRNA, and the transgene encoded by the first and the second vector is different.

In still other aspect, the protein encoded in the vector of the present method includes a porter protein, an antigen or a therapeutic protein.

In still other aspect, the reporter protein encoded in the vector of the present method includes fluorescent protein, beta-galactosidase, chloramphenicol acetyl transferase, human growth hormone, urease or alkaline phosphatase; wherein the antigen is derived from virulent pathogens; and wherein the therapeutic protein includes IL-12 or GM-CSF.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 5a to 5c, each represents a growth curve determined in a medium without any antibiotics; or a medium with kanamycin; or hygromycin, respectively. This confirms that kanamycin resistance gene contained in TOPO-pM90 vector of the present disclosure is properly working in cells. pSE100 is a control vector having a hygromycin resistance gene.

FIG. 10 is the results of FACS and microscopic analysis performed using *M. smegmatis* transformed with pM90-TOPO, Topo-pM90-EGFPh or Topo-pM90-EGFPe.

DETAILED DESCRIPTION OF THE EMBODIMENTS

Figure 1:
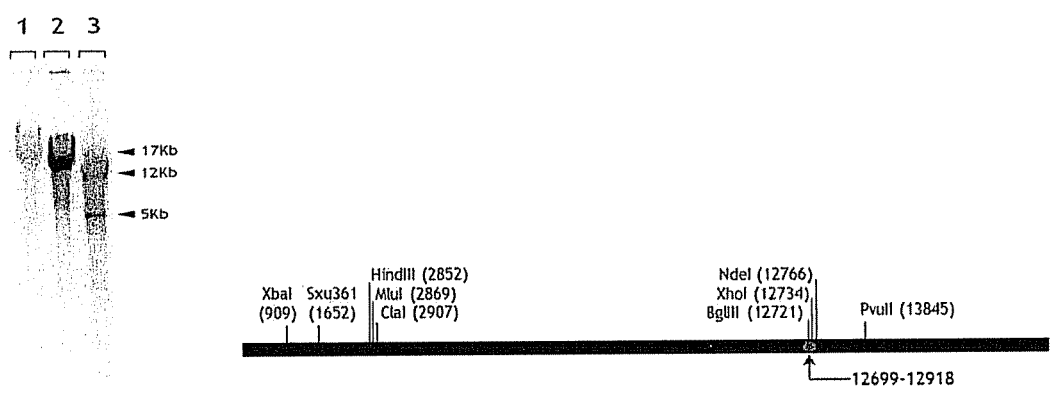
FIG. 1 is the agarose gel analysis result showing the genome from *Mycobacteria* and the genome digested with a restriction enzyme (left panel); and a schematic representation of the structure of the linear 18 kb plasmid pM90 (right panel). The each lane of the gel indicates: 1: genome of *M. intracellulare*; 2: genome of MOTT90; and 3: genome of MOTT90 digested with XhoI.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

The present inventors strived to develop a novel *Mycobacteria-Escherichia coli* shuttle vectors and identified a linear plasmid of about 18 kb in size comprising 16 open reading frames from *Mycobacteria* (for example 05-1390 strain) and a replication origin (designated as oriM) and Rep-like protein region which is required for replication.

Figure 2:
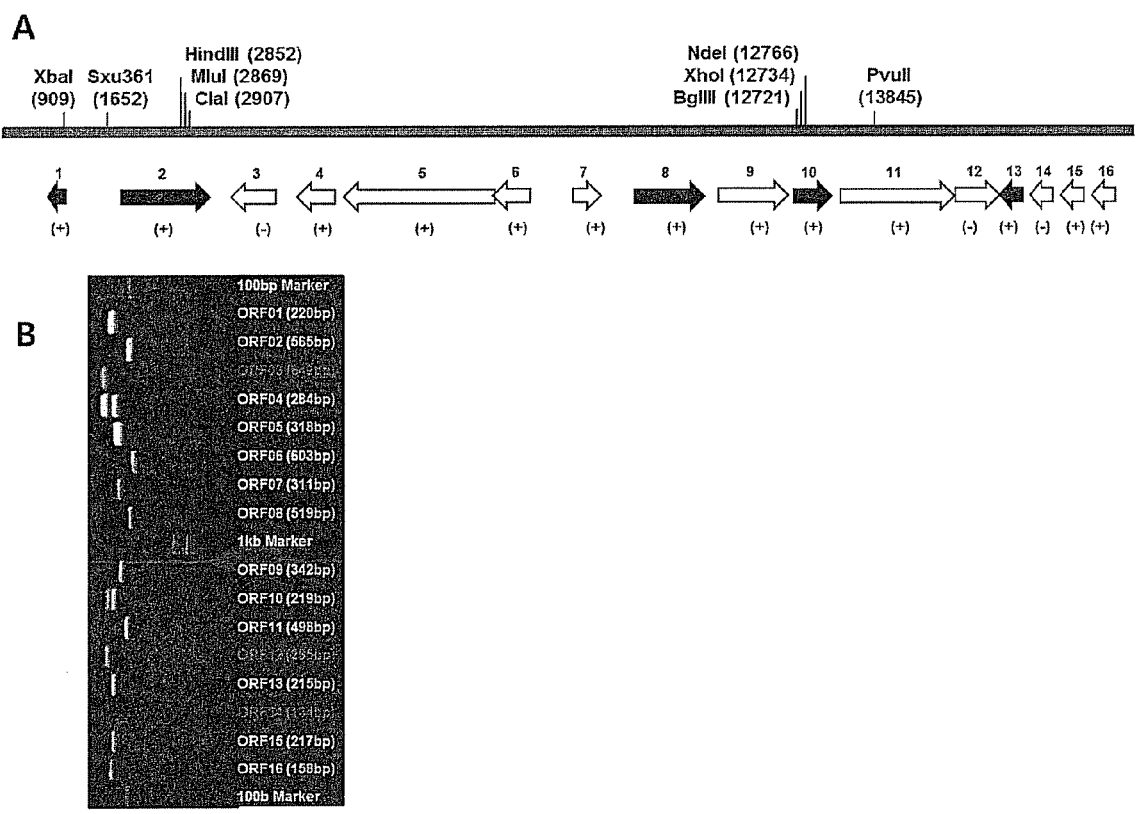
FIG. 2 is a schematic representation of the putative ORFs identified in the plasmid (A) in accordance of the present disclosure and the gel analysis result showing the expression from each ORF (B).
Figure 3:
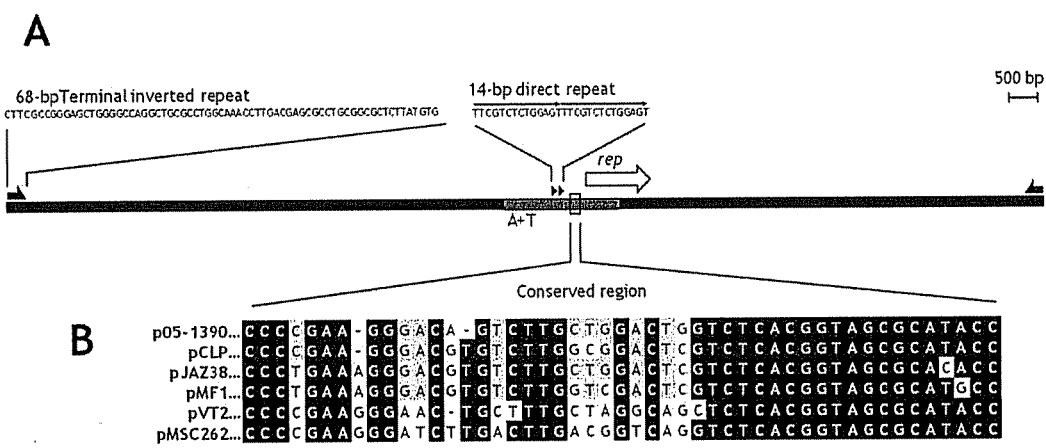
FIG. 3 is a schematic representation of the structure of the oriM of the plasmid in accordance of the present disclosure (A), which shows that the ori contains an AT-rich region, two 14 bp repeated regions that are disclosed as SEQ ID NO: 30 and a terminal inverted repeat of 68 bp, which is disclosed as SEQ ID NO: 29; and the alignment of the sequences of the conserved region from p05-1390, pCLP, pJAZ38, pMFI, pVT2 and pMSC262 (B), each of which is disclosed as SEQ ID NOs: 31, 32, 33, 34, 35 and 36, respectively.
Figure 4:
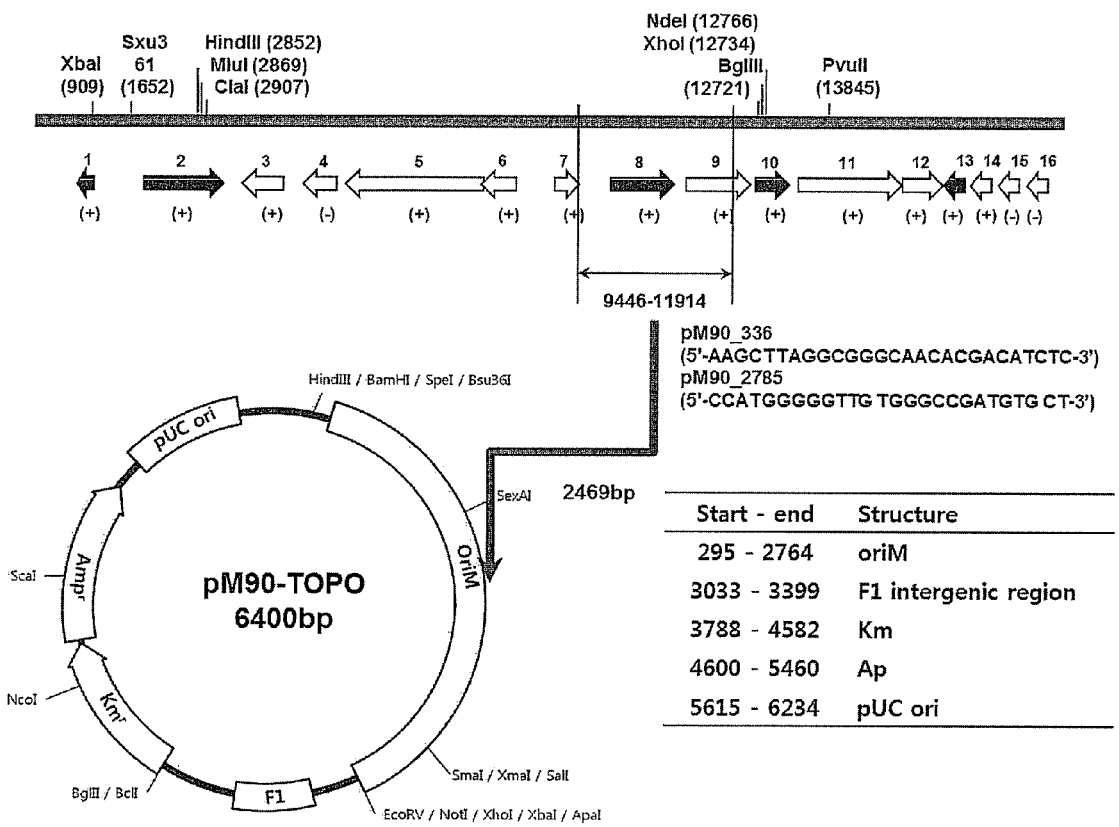
FIG. 4 is a schematic representation of the structure of Topo-pM90 vector. The oriM contained in pM90 was PCR amplified and was cloned into a TOPO TA vector.

In one aspect, the present disclosure relates to a plasmid from *Mycobacteria* and its use, and the plasmid of the present disclosure includes an origin of replication (oriM) and open reading frames (ORFs) including a protein such as rep-like protein and the like, which are required for the replication (refers to FIGS. 2 to 4). Therefore, the plasmid of the present disclosure is utilized as a gene and/or protein delivery system, and also in a therapeutic system such as immune therapeutics by effectively delivering DNAs and proteins into cells, in which they can function as antigens or therapeutic agents.

The term "transgene", "target material" or "heterologous expressible DNA encoded" as used herein are used interchangeably and refers to a desired heterologous DNA sequence or a gene introduced into the vector to be expressed in prokaryotes particularly in *Mycobacteria*, and/or in mammalian cells, including but not limited to genes or DNA sequences which may not normally be present in the genome, genes which are present, but not normally transcribed and translated ("expressed") in a given genome, or any other genes or DNA sequences which one desires to introduce into the genome.

In other aspect the present disclosure relates to a replicable DNA molecule derived from *Mycobacteria*, the DNA molecule having a nucleic acid sequence as disclosed in SEQ ID NO: 1. The DNA molecule contains nucleic acid sequences as disclosed in SEQ ID NOs: 3 to 15, whose corresponding amino acid sequences are disclosed as SEQ ID NOs: 16 to 28, respectively.

In still other aspect, the present disclosure relates to a *Mycobacteria-Escherichia coli* shuttle vector, the vector comprises an origin of replication designated as oriM having a sequence as disclosed in SEQ ID NO: 2. The *Mycobacteria-Escherichia coli* shuttle vector comprises: (a) an origin of replication having a nucleic acid sequence as disclosed in SEQ ID NO: 2 (oriM); (b) an origin of replication for prokaryotic cells; (c) a promoter; and (d) a nucleic acid sequence encoding a target material, which is operatively linked to the promoter.

In one exemplary embodiment, the nucleic acid sequence of oriM as disclosed in SEQ ID NO:2 contains a part of A+T rich region and direct repeat region. In particular, the oriM contains two 14 bp repeated regions (5'-TTCGTCTCTG-GAGT-3') in the AT rich region.

The plasmid or vector of the present disclosure can be constructed to be used as a vector for cloning or expression. Still the present vector can be constructed to be used in prokaryotic and/or eukaryotic cells as a host. In particular, the host for the present vector is prokaryotic cells in view of that the nucleic acid molecules of the present disclosure are derived from prokaryotic cells such as *Mycobacteria* and in consideration of the convenience of cell culture. For example, when the vector for the present disclosure is constructed as an expression vector and the host is a prokaryotic cells, the vector includes a strong promoter for transcription including such as tac promoter, lac promoter, lacUV5 promoter, Ipp promoter, PLλ promoter, PRλ promoter, rac5 promoter, amp promoter, recA promoter, SP6 promoter, trp promoter and T7 promoter, but the promoter is not limited thereto; a ribosomal binding site for initiating translation; and transcriptional/translational termination sites. When *E. coli* is used as a host cell, the regulatory elements which may be used for the present disclosure include but are not limited to operators and promoters for tryptophan biosynthesis in *E. coli* (Yanofsky, C., J. Bacteriol., 158:1018-1024 (1984)), and a leftward promoter of phage Lamda (PLλ promoter, Herskowitz, I. and Hagen, D., Ann. Rev. Genet., 14:399-445 (1980)).

The term "promoter" as used herein indicates DNA sequences which regulate the expression of sequences encoding a protein or a functional RNA. The nucleic acid sequences encoding a target material to be expressed are operatively linked to a promoter as described above. The term "operatively linked" as used herein indicates a functional link between a regulatory sequence for the expression of nucleic acids including, for example, promoter sequences, signal sequences, or transcription factor binding site, and other nucleic acid sequences. Here the regulatory sequence regulates the transcription or translation of the other nucleic acid sequences linked thereto.

The present vector system can be constructed using various methods known in the art. For example Sambrook et al., Molecular Cloning, A Laboratory Manual, Cold Spring Harbor Laboratory Press (2001) may be referred, the entire content of which is incorporated herein by reference.

In one preferred embodiment of the present disclosure, the cloning is practiced by Polymerase chain reaction (PCR). In one embodiment, the primes for the present discourse are used for gene amplification reaction.

PCR is a widely used method for amplifying nucleic acids and many modifications thereof are known in the art. For example, a touch down PCR, a hot start PCR, a nested PCR and booster PCR are developed to improve specificity or sensitivity of PCR. Also developed are real time PCR, differential display PCR, rapid amplification of cDNA ends, multiplex PCR, inverse polymerase chain reaction, vectorette PCR and thermal asymmetric interlaced PCR. A detailed explanation on PCR may be found in M. J., and Moller, S. G. PCR. BIOS Scientific Publishers, Springer-Verlag New York Berlin Heidelberg, N.Y. (2000), which is incorporated herein by reference.

The term "amplification reaction" as used herein refers to a reaction amplifying nucleic acid molecules. Various methods for amplification are known in the art, which for example include PCR (U.S. Pat. Nos. 4,683,195, 4,683,202, and 4,800,159), Reverse Transcription PCR (RT-PCR) (Sambrook et al., ibid), method as disclosed in WO 89/06700 by Miller, H. I. and EP 329,822 by Davey, C. et al., Ligase chain reaction (LCR) (Wiedmann M et al., 1994. PCR Methods Appl), Gap-LCR (WO 90/01069), repair chain reaction (EP 439,182), transcription-mediated amplification (TMA) (WO 88/10315), self-sustained sequence replication (WO90/06995), selective amplification of target polynucleotide sequences) (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid sequence based amplification (NASBA) (U.S. Pat. Nos. 5,130,238, 5,409,818, 5,554,517 and 6,063,603), but are not limited thereto. Other methods which may be used also described in U.S. Pat. Nos. 5,242,794, 5,494,810, 4,988,617 and application Ser. No. 09/854,317.

Also, the vectors of the present disclosure may be constructed using plasmids including such as for example pSC101, ColE1, pBR322, pUC8/9, pHC79, pUC19, pET and the like, phage such as for example, λgt4λB, λ-Charon, λΔz1 and M13 and the like, or virus such as for example SV40 and the like, which are known in the art.

In one exemplary embodiment, the promoter which may be used for the present vector includes, but is not limited to, a heat shock protein promoter, a CMV promoter, a promoter for 65 kDa common antigen of mycobacteria, ribsome RNA promoter from *Mycobacteria*, a promoter for MPB70, MPB59 or MPB64 antigen from *Mycobacterium bovis*, P1 promoter from bacteriophage Lamda, tac promoter, trp promoter, lac promoter, lacUV5 promoter, Ipp promoter, PLλ promoter, PRλ promoter, rac5 promoter, amp promoter, recA promoter, SP6 promoter, T7 promoter, a promoter for kanamycin resistance gene of transposon Tn903 or Tn5, a promoter for metallothionine, a growth hormone promoter or a hybrid promoter between eukaryotic and prokaryotic promoters, or a combination thereof.

The nucleic acid sequence encoding a target material to be expressed in cells includes any nucleic acid sequence of interest, which includes, but is not limited to, for example proteins such as reporter proteins, antigens and therapeutic proteins, and RNAs such as antisense oligonucleotides, siRNAs, shRNAs, miRNAs and piRNAs.

In one embodiment, the target material or transgene or heterologous expressible DNA encoded in the present vector may be translated into proteins in *Mycobacteria* and the translated products are then transferred to the eukaryotic cells of interest through Mycobacterial infection, in which case the transgene is operatively linked to a promoter suitable to direct the expression in prokaryotic cells, particularly in *Mycobacteria*. Examples of such promoters are as listed above. In other embodiment, the target material or heterologous expressible DNA encoded in the present vector may be translated in the eukaryotic cells where the target material is expected to work, in which case the transgene is operatively linked to a promoter suitable to direct the expression in eukaryotic cells. Examples of such promoters are as listed above. In either case, the heterologous expressible DNA or the transgene can provide an antigen or a therapeutic agent to the cells of interest.

In one illustrative embodiment, the antigen includes, but is not limited to, antigens which are used in vaccine therapies, for example, antigens from virulent pathogens such as hepatitis B virus (HBV) surface antigen, HBV core antigen, human immune-deficiency (HIV) gag protein and *Mycobacterium tuberculosis* Antigen 85A. The therapeutic proteins which may be encoded in the present vector include, but are not limited to, IL-12 or GM-CSF.

In one illustrative embodiment, the reporter protein includes, but is not limited to a fluorescent protein, beta-galactosidase, chloramphenicol acetyl transferase, human growth hormone, urease and alkaline phosphatase and the like.

In one exemplary embodiment, the fluorescent protein includes, but is not limited to, GFP (green fluorescent protein), RFP (red fluorescent protein), CFP (cyan fluorescent protein), YFP (yellow fluorescent protein), and BFP (blue fluorescent protein) and its variants.

The expression status and/or level of the reporter gene may be measured by various methods known in the art. For example, the methods for measuring the expression of luciferase, chloramphenicol acetyl transferase, beta-galactosidase, human growth hormone, and GFP may be found in de Wet J. et al, Mol. Cell. Biol., 7: 725-737 (1987), Gorman C. et al, Mol. Cell. Biol., 2: 1044-1051 (1982), Hall C. V. et al, J. Mol. Appl. Genet., 2: 101-109 (1983), Selden R. et al., Mol. Cell. Biol., 6: 3173-3179 (1986), Chalfie M. et al, Science, 263: 802-805 (1994), respectively.

In addition, the present vector may further comprise one or more selective markers. In one illustrative embodiment, the present vector may comprise genes encoding a protein conferring resistance to antibiotics, which include, but are not limited to, genes conferring resistance to kanamycin, hygromycin, ampicillin, streptomycin, penicillin, chloramphenicol, gentamicin, carbenicillin, geneticin, neomycin or tetracycline.

In one embodiment, the shuttle vector of the present disclosure may be used in a co-transformation with other vectors (for example, pAL 5000 vector) which have an origin of replication different from the shuttle vector of the present invention.

In other aspect, the present disclosure provides cells transformed with the present shuttle vectors.

Any cells known in the art which would be able to consistently clone and express the present vectors may be used. The host cells which may be transformed with the present vector include, but are not limited to, *E. coli* DH5α, *E. coli* JM109, *E. coli* BL21(DE3), *E. coli* RR1, *E. coli* LE392, *E. coli* B, *E. coli* X 1776, *E. coli* W3110, and *Mycobacterium* spp.

Methods to deliver the present vector to the cells are known in the art. For example, when the host cells are eukaryotes, CaCl2 precipitation method (Cohen, S. N. et al., Proc. Natl. Acac. Sci. USA, 9:2110-2114 (1973)), Hananhan's method (Hanahan, D., J. Mol. Biol., 166:557-580 (1983)) and/or electroporation method (Dower, W. J. et al., Nucleic. Acids Res., 16:6127-6145 (1988)) may be used.

In one exemplary embodiment, the cells which may be transformed with the present vector include *Mycobacteria* and *E. coli*. In other embodiment, *Mycobacteria* which may be transformed with the present vector include *M. smegmatis, M. bovis*-BCG, *M. avium, M. phlei, M. fortuitum, M. lufu, M. partuberculosis, M. habana, M. scrofulaceum*, and *M. intracellulare*. In another embodiment, *M. smegmatis, M. bovis*-BCG, *M. avium, M. partuberculosis, M. scrofulaceum*, and *M. intracellulare* are included. In still another embodiment, *M. smegmatis, M. bovis*-BCG, *M. avium* and *M. partuberculosis* are included. In still another embodiment, *M. smegmatis* and *M. bovis*-BCG are included.

In the present disclosure, the present vectors may be provided as a vaccine composition comprising: (a) a pharmaceutically effective amount of cells transformed with anyone of the present vectors; and (b) a pharmaceutically acceptable carrier. The term "pharmaceutically effective amount" refers to the amount sufficient to effecting the desired efficacy or activity of the cells transformed with the present vectors.

The target material which may be contained in the present vector to be expressed in cells includes antisense oligonucleotide, siRNA, shRNA and mRNA, but is not limited thereto.

The term "antisense oligonucleotide" as used herein refers to a DNA or RNA or derivatives thereof having a sequence complementary to mRNA, which inhibits translation of mRNA into a protein by binding to the complementary sequence in the mRNA. The antisense sequence of the present disclosure refers to a DNA or RNA, which has a sequence complementary to the target gene and thus be able to bind to the corresponding mRNA inhibiting the translation of mRNA into a protein, the translocation and/or maturation of mRNA or other essential biological functions. The length of the antisense oligonucleotides is about 6 bases to 100 bases, particularly about 8 to 60 bases, more particularly about 10 to 40 bases.

The term "siRNA" as used herein refers to a nucleic acid molecule which can mediate RNA hindrance or gene silencing (refer to WO 00/44895, WO 01/36646, WO 99/32619, WO 01/29058, WO 99/07409 and WO 00/44914). The siRNA can repress the expression of the target gene and thus is used in the field such as gene knock-down and gene therapy. siRNA which was originally discovered in plants, insects and fireflies and parasites now is used in mammalian cell research (Degot S, et al. 2002; Degot S, et al. 2004; Ballut L, et al. 2005).

The siRNA of the present disclosure may be double stranded having a sense strand and an antisense strand. In other embodiment, the siRNA of the present disclosure may be a single stranded which is self-complementary having a sense and antisense sequence in one strand.

The siRNA of the present disclosure is not limited to a complete match but includes ones containing a mismatch (the corresponding base is not complementary), a bulge (no corresponding base is present) and the like. The length of siRNA may be about 10 bases to 100 bases, particularly about 15 bases to 80 bases, more particularly about 20 to about 70 bases.

In the siRNA of the present disclosure, a short stretch of nucleic acid sequence of about 5-15 bases may be present between a sense and antisense sequence in self-complementary strand. In this case, the RNA transcribed from such nucleic acid sequences form a hair pin structure by intramolecular hybridization and takes a stem and loop structure. The stem and loop structure is processed in vitro and in vivo and generates siRNA molecules which mediate RNAi reaction.

The term "miRNA (micro RNA)" as used herein refers to a single strand RNA molecule of about 21 to 25 bases in length and regulates the expression of genes in eukaryotic cells by degrading mRNAs or inhibiting the translational process. The miRNA is produced by two step: in the first step, primary miRNA transcripts transcribed are processed to pre miRNA having a stem and loop structure of about 70-90 bases in length by an RNase III type enzyme called Drosha; in the second step, the pre miRNA migrates to the cytoplasm and further processed to produce a mature miRNA of about 21 to 25 bases digested by an enzyme called Dicer. The produced miRNA functions as a post transcriptional gene suppressor by complementary binding to a target sequence and thus induce mRNA instability and translational suppression. miRNAs are known to be involved in a variety of physiological functions and disease.

The term "piRNA (Piwi-interacting RNA)" as used herein refers to a single strand RNA molecule of about 26 o 31 bases in length and forms RNA-protein complexes through interactions with piwi proteins. It has been linked to both epigenetic and post-transcriptional gene silencing of retrotransposons and other genetic elements in germ line cells (Siomi M C et al., Nat Rev Mol Cell Biol., 12:246-258 (2011)).

The pharmaceutically acceptable carriers which may be included in the present composition include, but are not limited to, lactose, dextrose, sucrose, sorbitol, mannitol, starch, acasia gum, calcium phosphate, alginate, gelatin, calcium silicate, micro crystalline cellulose, polyvinylpyrrolidone, cellulose, water, syrup, methyl cellulose, methyl hydroxybenzoate, propylhyroxybenzoate, talc, magnesium stearate and mineral oil. The present composition may further includes lubricants, wetting agents, sweetening agents, flavors, emulsifier, suspending agents. The suitable pharmaceutically acceptable carrier and agents are described in detail in Remington's Pharmaceutical Sciences (19th ed., 1995).

The present composition may be formulated for example as a unit dosage form by using a pharmaceutically accepted carriers and/or excipients in accordance to the methods which may be practiced easily by one skilled in the art. The formulation may be powder, granulates, tablets, capsules or gel (such as hydrogel), which may further include dispersion agents or stabilizers.

In other aspect, the present disclosure relates to a method of using a first and a second vector for expression of heterologous transgenes in a eukaryotic cell, wherein the first vector is the vector according to the present disclosure and the second vector is pSE100 and its derivatives in eukaryotic cells.

The pSE100 vector is a Mycobacterial-Ecoli shuttle vector commercially available from addgene and is described in for example, Guo, X V, M Monteleone, M Klotzsche, A Kamionka, W Hillen, M Braunstein, S Ehrtand D Schnappinger (2007) Silencing *Mycobacterium smegmatis* by using tetracycline repressors. J Bacteriol 189(13): 4614-23. The present disclosure includes pSE100 or its derivatives. The derivatives for example include, but is not limited to, a vector having the same origin of replication as the pSE. The pSE is compatible with the present vector and can be used for two or more heterologous proteins. The transgenes which may be encoded by the vector used for the present method are as described above.

The present disclosure relates to a novel Mycobacteri-E. coli shuttle vectors and their uses. The plasmid of the present disclosure having a size of about 18 kb derived from *Mycobacteria* contains 16 ORFs, oriM and Rep-like protein essential for the replication. The plasmids of the present disclosure is useful in gene delivery system and research and also may be used in immune therapeutics by effectively delivering a nucleic acid sequence or recombinant protein.

The present disclosure is further explained in more detail with reference to the following examples. These examples, however, should not be interpreted as limiting the scope of the present invention in any manner.

EXAMPLES

Materials and Methods
Cells and Cell Culture

For the amplification of plasmids, *E. coli* DH5α strain (RBC) was used. The *E. coli* cells grown at 37 in LB medium were heat shocked at 42 for transformation with plasmids. The cells transformed with the plasmids were then selected by growing the cells in a medium containing an antibiotic. The selected colonies were then cultured and the plasmids in the cells were extracted using PureLink™ HiPure Plasmid Filter Maxiprep Kit (Invitrogen, USA) in accordance with the manufacturer's instruction. The sample from a patient 05-1390, *M. smegmatis* MC2155 and Mycobacterial strain BCG-Japan were grown at 37 in a 7H10 liquid medium or a 7H10 solid medium, which were transformed with the plasmid using an electroporation method.

Extraction of DNA from 05-1390

Mycobacterial strain 05-1390 was inoculated onto a 7H10 solid medium and allowed to form a colony by incubating it at 37. The colonies were picked using a loop and suspended in 400 μl of TE (Sigma, USA) in a 1.5 ml tube. The cells were then treated at 80 for 10 min to kill *Mycobacteria*. Then 10 mg/ml of lysozyme (Roche diagnostics, USA) was added thereto and incubated at 37 for 1 hour. 70 μl of 10% SDS (USB, USA) and 5 μl of 10 mg/ml proteinase K (Bioline, USA) was added and mixed by vortexing and incubated at 65 for 10 min. 750 μl of chloroform/isoamyl alcohol (Sigma, USA) (24:1, v/v) was added and vortexed for 10 sec and centrifuged at RT for 5 min at 12,000×g. Then 180 μl of the supernatant was then transferred to a new tube and 450 μl of isopropanol was added and the mixture was incubated for 30 min at −20. The DNA contained in the mixture was then precipitated by centrifugation at 12,000×g for 15 min at 4. The precipitated DNA was then washed using 70% alcohol at 4 and centrifuged at 12,000×g for 5 min at 4 to remove the supernatant. The pellet was then air dried and dissolved in 200 μl of TE.

Southern Blotting and Western Blotting

To confirm the presence of a linear plasmid in 05-1390 sample, High prime DNA labeling and detection starter kit II (Roche diagnostics, USA) was used to extract the genome in accordance with the manufacturer's instruction. The genome DNA was then electrophoresed on a 1% agarose gel (Bioline) at 100V for 3 hours. The agarose gel was immersed and rocked in 400 ml of 0.25 M HCl (Junsei, Japan) solution for 20 min. The HCl solution was removed from the gel and the gel was immersed and rocked in 400 ml of 0.5M NaOH (Junsei)/1.5M NaCl solution for 20 min followed by another 20 min incubation in a 1.5M NaOH (Junsei)/1.5M NaCl solution. The buffer was then removed and the gel was blotted with 3 sheets of filter papers (Whatman, USA) presoaked with 10×SSC. A nylon membrane (Amersham, USA) having the size of the gel was placed onto the gel and 3 sheets of filter papers (Whatman) was placed on top of the nylon membrane. And the paper towel was stacked on the filter paper in 10 cm thick and was pressed with a weight of about 400 g. The entire stack was then wrapped with a plastic film to prevent evaporation and left for 24 hours at RT. After that, the DNA transferred to the membrane was cross-linked at 120 mHcm-2 using a UV cross linker. The membrane was then immersed in DIG Easy Hybridization solution (Roche diagnostics USA) pre-equilibrilized at 37 in a tube and rocked for 15 min at 42. The probe prepared by PCR was boiled for 5 min and cooled down in ice and added to the membrane in the DIG Easy Hybridization solution as prepared above at 37. The DNA probe (342 bases) was prepared by PCR using PCR DIG Probe Synthesis Kit (Roche diagnostics) in accordance with the manufacturer's instruction from 05-1390 gDNA. The primers used as follows: sense (ORF9_F): 5'-gcggtgccacagt-gccagtag-3'; and antisense (ORF9_R): 5'-tcatggacgaagccga-cagagc-3'. After the hybridization, the membrane was washed 2× for 5 min each with 2×SSC/0.1% SDS solution followed by washing 2× for 15 min each with 0.5×SSC/0.1% SDS.

For western blotting, the membrane as prepared above was washed for 1 to 5 min in 0.1 M maleic/0.15 M NaCl/0.3% Tween®20 solution. Then the membrane was washed in a blocking solution (10× blocking solution:maleic acid=1:10) for 30 min. The blocked membrane then was immersed and rocked in a solution containing antibody, which was then washed twice for 15 min each in 100 ml of 0.1M maleic acid/0.15M NaCl/0.3% Tween®20. The membrane was then incubated with 20 ml of detection solution for 2 to 5 min at RT. Then 1 ml of CSPD (Roche diagnostics) was spread onto the membrane and covered with a plastic film to prevent from drying. After that, the excess liquid was removed from the membrane and left for 10 min at 37 and the fluorescent signal was read using Las4000 (Fujifilm, Japan).

Results

The Confirmation of a Novel Linear Plasmid in a New Strain 05-1390

The genome from *M. intracellulare* and *Mycobacterium* MOTT90 were extracted and southern-blotted as described above. The results are shown in FIG. 1, which indicated the presence of a plasmid of about 18 kb in size only in *Mycobacterium* MOTT90 and the linear plasmid was confirmed by two bands after digestion with Xho I.

ORF Search and Sequence Analysis

ORF finder program from NCBI (http://www.ncbi.nlm.nih.gov/projects/gorf/) was used to search putative ORFs in 05-1390 linear plasmid (18090 kb) encoding 150 amino acids in length at the least. The 16 ORFs identified using the program was compared with the linear plasmid sequence from *M. celatum* using the Blast search. As a result, a total of 16 ORFs were found to be present in the plasmid of the present disclosure. As described in Table 1, out of 16 ORFs present in the plasmid, the rep-like protein essential for replication was confirmed to be present.

TABLE 1

Genes found in pM90 and analysis of sequence homology

| ORF No. | Expected length (aa) | identity (%) | The nearest homolog (homolog) (species and strain or plasmid) | Known or potential function | Accession No. |
|---|---|---|---|---|---|
| 1 | 134 | 68 | *Streptosporangium roseum* | ATP-dependent protease Clp ATPase subunit like protein | YP_003336723.1 |
| 2 | 493 | 95 | *Mycobacterium tuberculosis* | Transposase | NP_217307.1 |
| 3 | 264 | 100 | *Mycobacterium* sp. MCS plasmid 1 | hypothetical protein | YP_642699.1 |
| 4 | 200 | 65 | *Aspergillus oryzae* RIB40 | hypothetical protein | XP_001816628.2 |
| 5 | 806 | 54 | *Mycobacterium* sp. MCS plasmid 1 | hypothetical protein Mmcs_5513 | YP_642669.1 |
| 6 | 209 | 86 | *Mycobacterium* sp. MCS plasmid 1 | hypothetical protein Mmcs_5514 | YP_642670.1 |
| 7 | 121 | 85 | *Mycobacterium* sp. MCS plasmid 1 | hypothetical protein Mmcs_5516 | YP_642672.1 |
| 8 | 416 | 70 | *Mycobacterium celatum*, pCLP | Rep-like protein | NP_862580.1 |
| 9 | 364 | 62 | *Mycobacterium vanbaalenii* PYR-1 | hypothetical protein Mvan_3735 | YP_954523.1 |
| 10 | 217 | 97 | *Mycobacterium celatum*, pCLP | ParA-like protein | NP_862577.1 |
| 11 | 629 | 98 | *Mycobacterium gilvum* PYR-GCK, pMFLV01 | hypothetical protein Mflv_5560 | YP_001136809.1 |
| 12 | 243 | 85 | *Mycobacterium gilvum* PYR-GCK, pMFLV01 | hypothetical protein Mflv_5561 | YP_001136810.1 |
| 13 | 108 | 99 | *Mycobacterium smegmatis* | pemK-like protein MazF | YP_888722.1 |
| 14 | 76 | 90 | *Methylobacterium nodulans* | hypothetical protein Mnod_1051 | YP_002496361.1 |
| 15 | 176 | 67 | *Mycobacterium abscessus* | hypothetical protein MAB_0782 | YP_001701532.1 |
| 16 | 60 | 96 | *gliobacterium violoacea* | Methionine adenosyltransferase | NP_926067.1 |

As described in Table 1, out of 16 ORFs present in the plasmid, the rep-like protein essential for replication was confirmed to be present.

Characterization of the Linear Plasmid at Molecular Biological Level 05-1390 Total RNA Extraction from 05-1390

The 05-1390 cells was cultured to the exponential phase in 100 ml of a 7H9 medium at 37. The cell culture was centrifuged at 3000×g for 15 min at 4 and the supernatant was decanted and the precipitated cells were mixed with 1 ml of RNAprotect bacterial reagent (Quiagen, USA). Then, the mixture was washed by centrifugation at 3000×g for 15 min at 4. 1 ml of TRIsure regent (Bioline) and 0.1-mm glass beads were added to the obtained cells, which were then disrupted at a bead beater (BioSpec, USA) at 5000 rpm for 40 sec. The tube was then immediately transferred to ice and left for 5 min. 0.25M chloroform solution was added to the tube and vortexed for a few seconds and the cells were left for 2 min at RT, which was then centrifuged at 12,000×g for 15 min and the supernatant was transferred to a new tube and mixed with 0.5 ml of isoprorpanol and left for 15 min at RT. The mixture was then centrifuged at 12,000×g for 15 min and the supernatant was removed and the pellet was washed with 1 m of 75% ethanol by centrifugation at 12,000×g for 5 min. The supernatant was removed and the RNA pellet was air dried for 5 min at RT. The pellet was dissolved in ddH2O treated with DEPC (diethyl polycarbonate; Bioline) and kept was at −20 before use.

The Confirmation of Transcription from the ORFs by RT-PCR (Reverse Transcription-Polymerase Chain Reaction)

The total RNA extracted as above was reverse transcribed and amplified using ONE-STEP RT-PCR PreMix Kit (IN-TRON, Korea) in accordance with the manufacturer's instruction. The PCR primers used were designed 19 to 25 bases in length to amplify ORFs of 134 to 685 bp in length as described in Table 2. 8 μl of ONE-STEP-RTPCR PreMix Kit, 100 ng of total RNA, 0.5 μM of sense and antisense primer was mixed in a total volume of 20 μl in ddH2O. PCR was performed in a thermal cycler 9700 (Applied Biosystems, USA) at the condition of pre-treatment at 45 for 30 min; 30 cycles of 30 sec at 94 and 30 sec at 60 and 1 min at 72; and final extension for 5 min at 72; and soaking at 4. The PCR products were analyzed by electrophoresis on a 1% agarose gel followed by visualization with ethidium bromide illuminated with UV light.

TABLE 2

ORFs found in the present plasmid and primers used for the amplification.

| ORF No. | Expected Protein (aa) | Sequence (5'->3') | | size (bp) |
|---|---|---|---|---|
| | | Sense primer | Antisense primer | |
| 1 | Clp domain protein | GCTACGCCGCACTACCTTTAT | GTGTTTGACGAGCTGACGAGTG | 520 |
| 2 | Transposase | CGCCTCGGCTCCCATTGTC | TGGTGGCCCGCAGACATTC | 631 |
| 3 | Hypothetical protein | ACGCGCTGGTAGTGCTCCCTTAG | CGAACACAAGCGCGACCACTACA | 262 |
| 4 | unknown | CCTCGGCGGCGTAGTCAGTCA | GCCGGCCATATCACGATTCATTAC | 295 |
| 5 | Hypothetical protein Mmcs_5513 | TTCCACCCGCGGCATCGTA | GCGCCGCCGAGCAATACA | 275 |
| 6 | Hypothetical protein Mmcs_5514 | CTTGCTTTCGAGGTCTTTGA | GCAACGCGCCGCCGAGCAATAC | 603 |
| 7 | Hypothetical protein Mmcs_5516 | TGGATCAGGCCCGTAGGACA | TCATGGACGAAGCCGACAGAGC | 665 |
| 8 | Rep-like protein | GCGGTGCCACAGTGCCAGTAG | TCATGGACGAAGCCGACAGAGC | 342 |
| 9 | Hypothetical protein Mvan_3735 | ACACGGCGATCACGGGCTTAT | CGAGACACCATCCACCGAGAAAT | 197 |
| 10 | ParA-like protein | CCGCTGCCGCACGAATACAT | CGTTGGCGGTCGATTCTTCACT | 477 |
| 11 | Hypothetical protein Mflv_5560 | GTTCGGTGCGGCGTTCAAG | GGCGGGCGAACTGGTCAATAC | 290 |
| 12 | Hypothetical protein Mflv_5561 | GCGCAGCGGGCAATGGAG | ACACCCGCACCCCGTCTC | 285 |
| 13 | pemK-like protein, MazF | TCCGAGGAAGACGAGTAGG | TCCGTCACAATCTGCCCCCTCACA | 215 |

TABLE 2-continued

ORFs found in the present plasmid and primers used for the amplification.

| Expected ORF No. | Protein size (aa) | Sequence (5'->3') Sense primer | Antisense primer | size (bp) |
|---|---|---|---|---|
| 14 | Hypothetical protein Mnod_1051 | GCGGAGATGGCATCCAC | GCTACGCCCCCTTCAAATA | 134 |
| 15 | Unknown | CGGGTGAGTCTTGGCGGCGGGGTA | ATCTCGTGCACGTAGAAGGAAA | 187 |
| 16 | Unknown | TTCTGTGTCGCCTATGCGGCCGGC | TCTGGCGATCGTGAAGACGAGCAC | 174 |

Of the total 16 putative 16 ORFs, 13 ORFs except 12 and 14 was confirmed to be transcribed using RT-PCR (FIG. 2). The analysis of the entire plasmid revealed the presence of the AT rich region and direct repeat region (FIG. 3).

The Amplification of oriM of the Linear Plasmid

Using 05-1390 genomic DNA as a template, the 2,469 bp region identified to contain oriM corresponding to the bases from 9,466 to 11,914 was amplified suing primers: p05-1390.sub.—336(5'-AAGCTTAGGCGGGCAACACGA-CATCTC-3': SEQ ID NO: 37) and p05-1390.sub.—2785(5'-CCATGGGGGTTGTGGGCCGATGTGCT-3': SEQ ID NO: 38). The PCR conditions were as follows: 1 cycle of pre-denaturation step of 2 min at 94 .degree. C.; 30 cycles of amplification step of 30 sec at 95 .degree. C. and 30 sec at 65 .degree. C. and 4 min at 95 .degree. C.; and 1 cycle of final extension step for 10 min at 72 .degree. C. 1 .mu.l of PCR product, 1 .mu.l of TOPO TA vector (Invitrogen, USA). 1 .mu.l of TA cloning buffer and 3 .mu.l of ddH2O were mixed and left for 5 min at RT. The 7 .mu.l of reaction product was mixed with 50 .mu.l of E. coli DH5.alpha. (RBC) competent cells and heat shocked for 45 sec at 42 .degree. C. Then 250 .mu.l of SOC medium was added and the mixture was left for 1 hour at 37 .degree. C. 80 .mu.l of the mixture was then spread on to a LB agar plate containing Kanamycin (100 .mu.l/ml) and IPTG, which was incubated at 37 .degree. C. for 16 hours. The colonies formed were then analyzed by PCR for the presence of the plasmid of interest using the primers as described above and analyzed on a 1% agarose gel. The results are shown in FIG. 4.

The Stability of TOPO 05-1390 and Compatibility with pSE100

Preparation of Competent Cells of Mycobacteria 2.5 liters of M. smegmatis cells competent for electroporation was cultured to have an O.D. of 0.8 to 1.0 at 600 nm and cooled down for 2 hours on ice. The culture was then centrifuged at 3,000×g for 5 min and suspended and sequentially washed with 20 ml, 10 ml and 5 ml pf 10% glycerol by centrifugation at 3,000×g for 5 min. After the final washing step the cells were suspended at 5 ml of 10% glycerol, the 1/500 volume of the initial culture volume. The 200 µl aliquot of the competent cell's was prepared in a 1.5 ml eppendorf tube and kept at −70 until use.

The Stability of TOPO 05-1390

The 200 µl of the competent cells as prepared above was thawed slowly on ice and then mixed with 5 µg of TOPO05-1390 or pSE100 and the mixture was left on ice for 20 min. The mixture was then transferred to a 0.2 cm cuvette (Bio-Rad, USA) kept cold on ice and the electric field was applied for 25 µF, 2.50 kV and 1000Ω using Gene pulser and pulse controller accessories from Bio-Rad and left for 5 min on ice. The cells were then added to 5 ml of a 7H9 liquid medium in a 15 ml tube and cultured for 4 hours at 37. For TOPO05-1390, 1/100 dilution of the culture was spread onto a LB agar plate containing kanamycin (20 µl/ml) and incubated for about 7 to 10 days at 37 until colonies were formed. For pSE100, 1/100 dilution of the culture was spread onto a LB agar plate containing hygromycin (50 µl/ml) and incubated for about 7 to 10 days at 37 until colonies were formed. After that, a transformed colony (TOPO05-1390 and pSE100) was picked and inoculated to 5 ml of 7H9 liquid medium for 5 days, during which at every 24 hours, 1/100 dilution of the culture was spread onto a LB agar plate containing corresponding antibiotics and a LB agar plate without antibiotics and the number of colonies were counted and compared.

Figure 5:
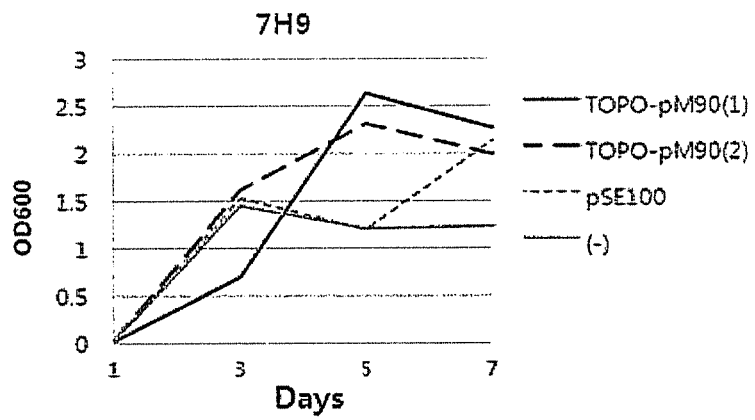
FIG. 5 is the results of an assay to determine the growth pattern of *M. smegmatis* transformed with Topo-pM90.
Figure 5:
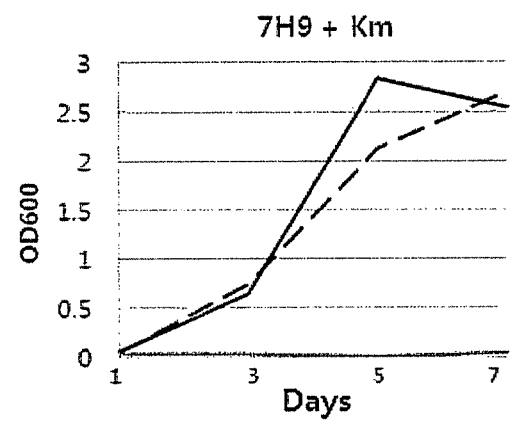
Figure 5:
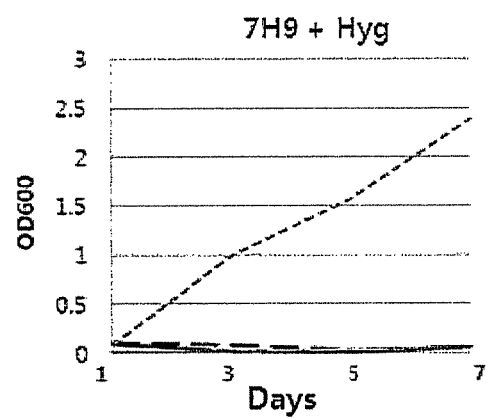

The results are shown in FIG. 5. The transformed cells containing the recombinant plasmid of the present disclosure, TOPO-pM90, grew well both in the regular medium without antibiotics and also in the medium with kanamycin. This indicates that TOPO-pM90 maintains the resistance to kanamycin (FIGS. 5a and 5b). For hygromycin, only pSE100 used as control shows resistance to hygromycin (FIG. 5c). The results confirm that the kanamycin resistance gene contained in TOPO-pM90 functions properly in cells.

Figure 6:
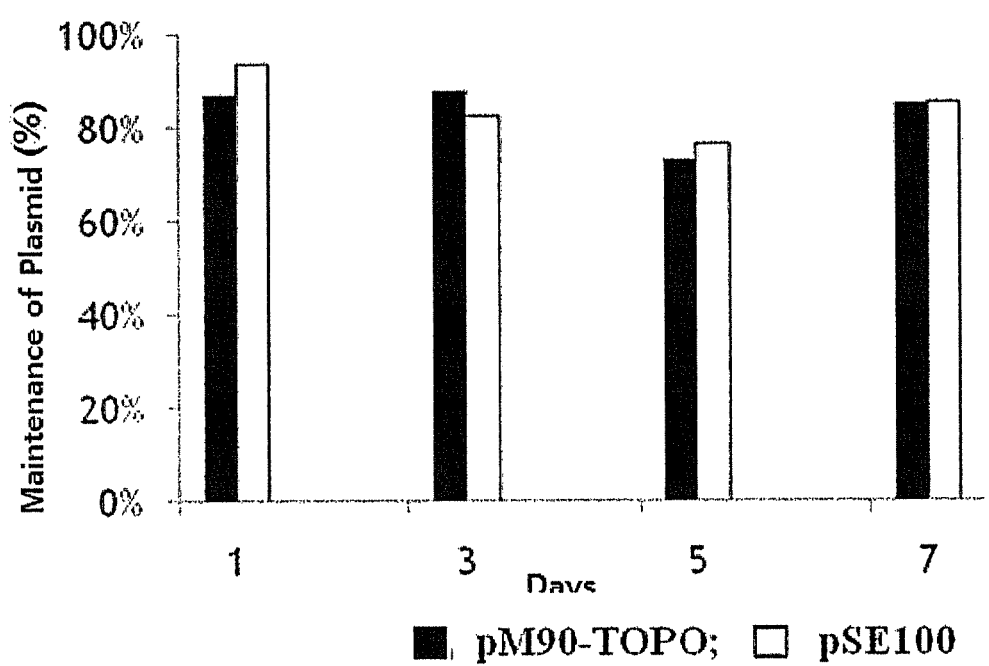
FIG. 6 is the results of an assay to determine the stability of Topo-pM90 transformed into *M. smegmatis*. During the 7 day incubation period, the stability of the present vector (■, pM90-TOPO) was similar to that of the control vector (□, pSE100).

Also, the stability of M. smegmatis transformed with pM90-TOPO was found to be similar to that of pSE100 during the 7 day incubation period (FIG. 6).

Figure 7:
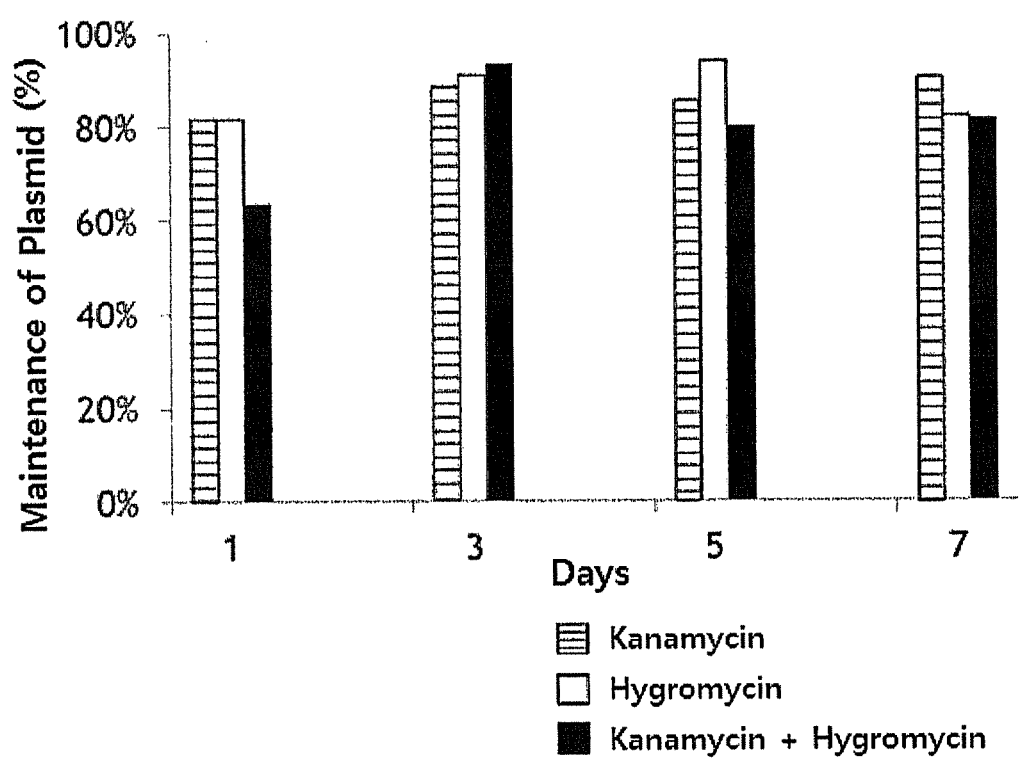
FIG. 7 is the results of an assay to determine the compatibility of pSE100 and pM90-TOPO. The two plasmids were co-transformed into *M. smegmatis* and were cultured in a medium containing antibiotics. The results shows that the ability of the transformed cells to grow in a medium containing all the antibiotics tested (▤ : Kanamycin; □: Hygromycin; ■: Kanamycin plus Hygromycin)

Compatibility with pSE100 pM90-TOPO and pSE100 was co-transformed into M. smegmatis using as described above. The colonies formed/cultured were inoculated into a 5 ml of 7H9 liquid medium containing kanamycin (20 µl/ml) and hygromycin (50 µl/ml) and incubated for about 7 days at 37, during which at every 24 hours, 1/100 dilution of the culture was spread onto a LB agar plate containing the above antibiotics and a LB agar plate without antibiotics and the number of colonies were counted and compared. The results as shown in FIG. 7 indicates the compatibility between pM90-TOPO and pSE100.

The Construction of a Shuttle Vector Using pM90-TOPO TOPO05-1390EGFPh

Figure 8:
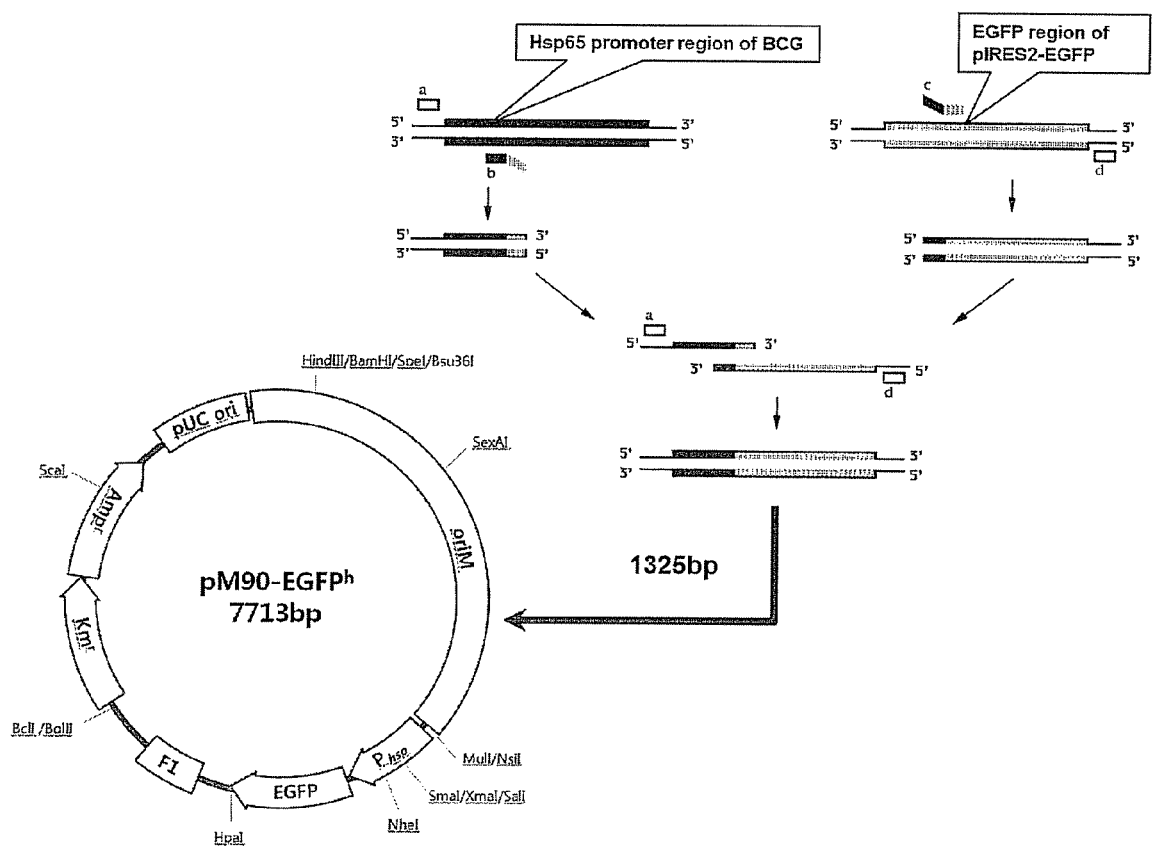
FIG. 8 is a schematic representation showing the construction process of Topo-pM90-EGFPh. HSP60 promoter and EGFP fragments were amplified by PCR and then the two fragments were fused using a sense primer for HSP60 and a reverse primer for EGFP. The fused fragment was then ligated into pTopo05-1390 to produce pM90-EFGPh vector.

HSP promoter fused with EGFP gene was inserted into TOPO05-1390 by PCR (FIG. 8) using pIRES2-EGFP as a template. The primers used were: sense prime; 5'-ATCCG-GAGGAATCACTTCGCAATGGCCACAAC-CATGGTGAGC-3'), which contains at its 5' end the 20 bp promoter region corresponding to the end of HSP 60 promoter from M. bovis and reverse primer; 5'-CCCGATATCT-TACTTGTACAGCTCGTCCA-3', which encodes at its 3' end an EcoRV restriction site. The PCR conditions as follows: 1 cycle of pre-denaturation step at 94 for 2 min; 30 cycles of amplification step at 95 for 30 sec and at 65 for 30 sec and at 72 for 1 min; and 1 cycle of a final extension step at 72 for 10 min. The amplified products war run on a 1% agarose gel and purified by PCR quick spin kit (Intron). The purified product was then digested with EcoRV (NEB, USA) at 37 for 16 hours and isopropanol was added thereto and the mixture was incubated at −20 overnight to precipitate DNA. The precipitated product was then centrifuged at 13,000 rpm for 15 min and the pellet was washed once with 300 μl of 70% ethanol and the washed pellet was air dried and dissolved in TE (201). The TOPO05-1390 was digested with EcoRV as above and the digested DNA was treated with CTAP (1 μl) at 37 for 15 min and 55 for 15 min. The process to precipitate the DNA was done as described above. The constructed hsp-EGFP and TOPO05-1390 was mixed at 3:1 ratio, which then was mixed with T4 DNA ligase (1 μl) and incubated for 4 hours at 4. After that the ligated product (1 μl) was added to E. coli DH5α (RBC) the competent cells followed by heat shock for 45 sec at 42. After the heat shock, 250 μl of SOC medium was added to the cells followed by incubation at 37 for 1 hour. After the incubation, 80 μl of the cells was spread onto a solid LB agar plate containing kanamycin (100 μl/ml) and incubated at 37 for 16 hours. The colonies formed was picked and was used for PCR using the corresponding primer set as described above and the ligated product was confirmed on a 1% agarose gel.

TOPO05-1390EGFPe

Figure 9:
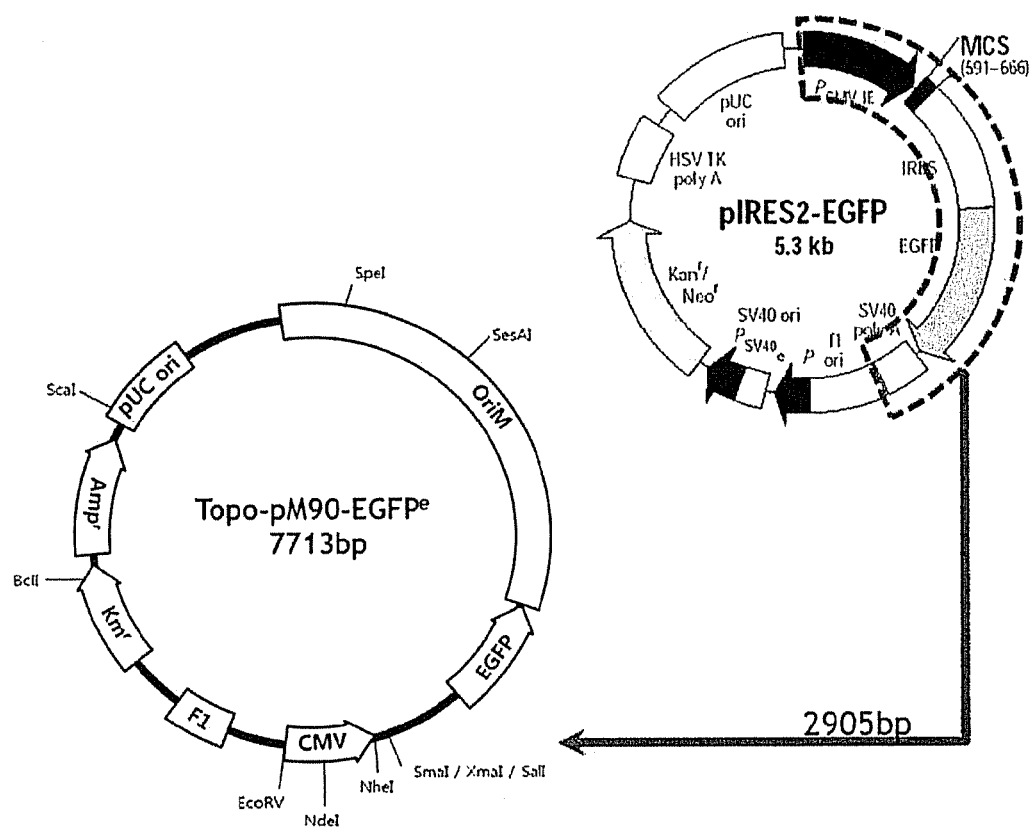
FIG. 9 is a schematic representation showing the construction process of Topo-pM90-EGFe. pIRES2-EGFP was digested with NsiI and ligated to a pTopo05-1390 digested with NsiI and treated with CIAP to produce Topo-pM90-EGFe vector.

EGFP gene construct having a CMV promoter was inserted into TOPO05-1390 (FIG. 9). In detail, pIRES-EGFP (1 μg) was digested with NsiI (NEB) at 37 for 16 hours. The restricted product was run on a 1% agarose gel and the 2,095 bp fragment corresponding from CMV to polyA tail was purified from the gel by using gel extraction kit (Qiagen, USA). TOPO05-1390 plasmid was digested as described above for pIRES-EGFP was treated with CIAP (1 μl) at 37 for 15 min and 55 for 15 min. The process to precipitate the DNA was done as described above. The pIRES2-EGFP_2095 bp and TOPO05-1390 was mixed at 3:1 ratio, which was then mixed with T4 DNA ligase (1 μl) and incubated for 4 hours at 4. After that the ligated product (1 μl) was added to E. coli DH5α (RBC) the competent cells followed by heat shock for 45 sec at 42. After the heat shock, 250 μl of SOC medium was added to the cells followed by incubation at 37 for 1 hour. After the incubation, 80 μl of the cells was spread onto a solid LB agar plate containing kanamycin (100 μl/ml) and incubated at 37 for 16 hours. The colonies formed was picked and used for PCR using the corresponding primer set as described above and the ligated product was confirmed by electrophoresis on a 1% agarose gel.

Confirmation of Protein Expression from the Recombinant Vector in Mycobacteria

Each of pM90-EGFPh (5 μg) and pM90-EGFPe (5 μg) constructed as described above was used for transformation into Mycobacteria as described above. The cells were spread on the LB agar plate containing kanamycin (100 μl/ml) and incubated for 10 days. After 10 days, a colony was inoculated into a 3 ml of 7H9 liquid medium and incubated and passaged every 3 days. The cells were then observed using Fluorescent microscope (Olympus), confocal microscopy (Olympus) or FACS (BD science) for GFP expression.

Figure 10A:
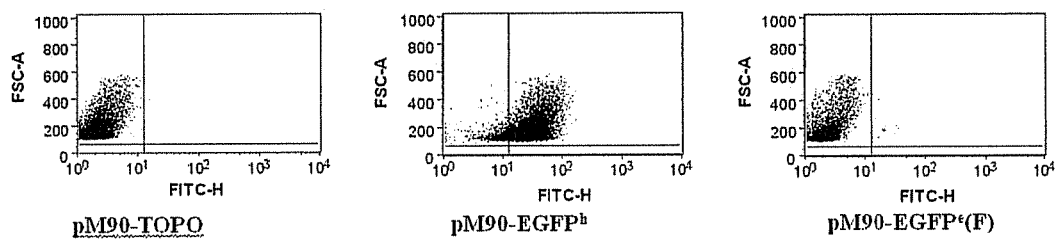
FIG. 10a represents a FACS result showing the fluorescence from GFP.
Figure 10B:
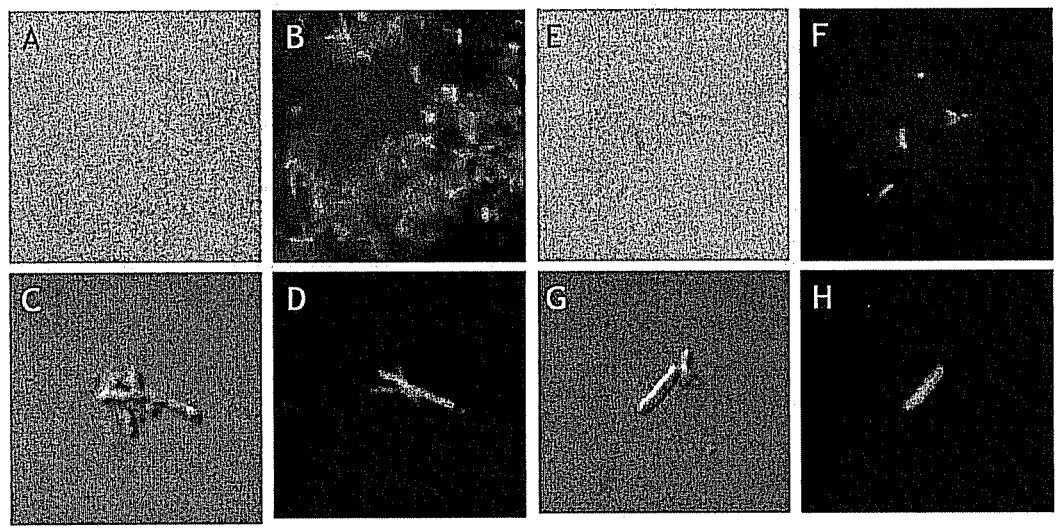
FIG. 10b shows the GFP fluorescence within a cell observed using an optical microscope (A, B, E, and F) or a confocal microscope (C, D, G, and H).
Figure 11:
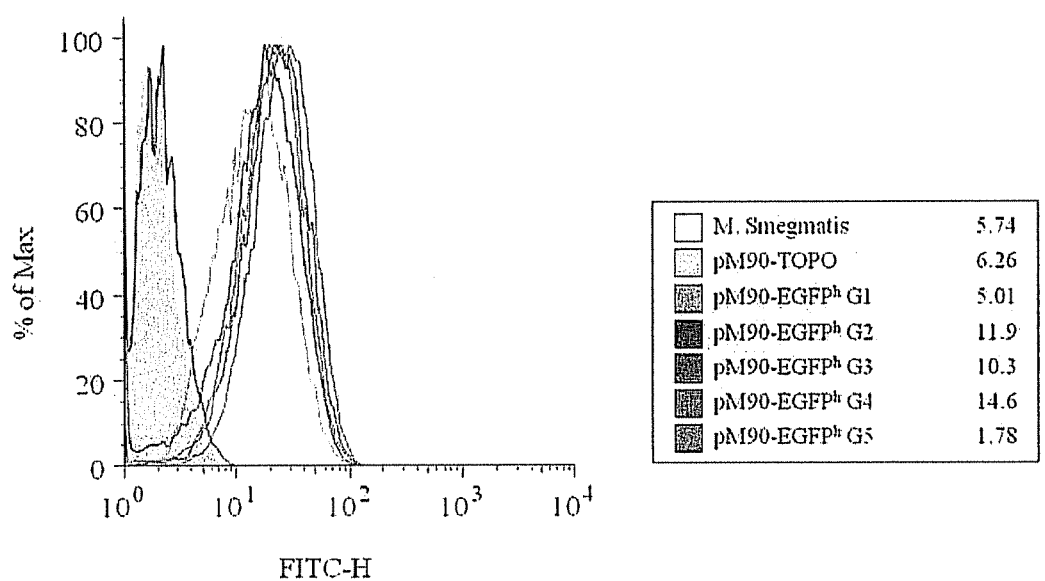
FIG. 11 is the FACS analysis results showing that Topo-pM90-EGFPh of the present disclosure have a better GFP expression level and a better vector stability compared to pAL5000 vectors in *M. smegmatis*.

To confirm GFP expression in the cells, for pM90-EGFP$^h$, the cells at the 4 passages were used for microscopic examination. For FACS, 500 μl of the cells at the 4 passages was washed twice with 500 μl of PBS and then resuspended with 1 ml of PBS and used for GFP. Mycobacterium smegmatis transformed with pM90-EGFP$^h$, pM90-EGFP$^e$ or pM90-TOPO was analyzed by FACS. The results showed that the fluorescent signal was not detected in EGFPe or pM90-TOPO but was detected in pM90-EGFPh cells (FIG. 10a). The fluorescent signal from pM90-EGFPh was detected in Mycobacterium smegmatis (A, B, C, D) and BCG (E, G, F, H)(FIG. 10b). This indicates that the stability of GFP expression in Mycobacterium smegmatis was better compared to the conventional pAL5000 vector (FIG. 11).

Confirmation of Protein Expression from the Recombinant Vector in Eukaryotic Cells Each of pM90-EGFPh (5 μg) and pM90-EGFPe (5 μg) constructed as above was used for transformation into Mycobacteria as described above. The transformed Mycobacteria was diluted in DMEM with 10% FBS at 10, 50 or 100 MOI (multiplicity of infection) and 1 ml of the diluted cells was then used to infect J774 cells (ATCC TIB-67), which were prepared 24 hours in advance at $3 \times 10^5$ cells/well of a 12 well plate for 1 hour. After the infection, gentamycin (10 μg/μl, Sigma) was added thereto to remove Mycobacteria. After one hour, the medium was replaced with DMEM containing 10% FVS without an antibiotics and the cells were examined using FACS, confocal microscope and fluorescent microscope for GFP expression.

Figure 12:
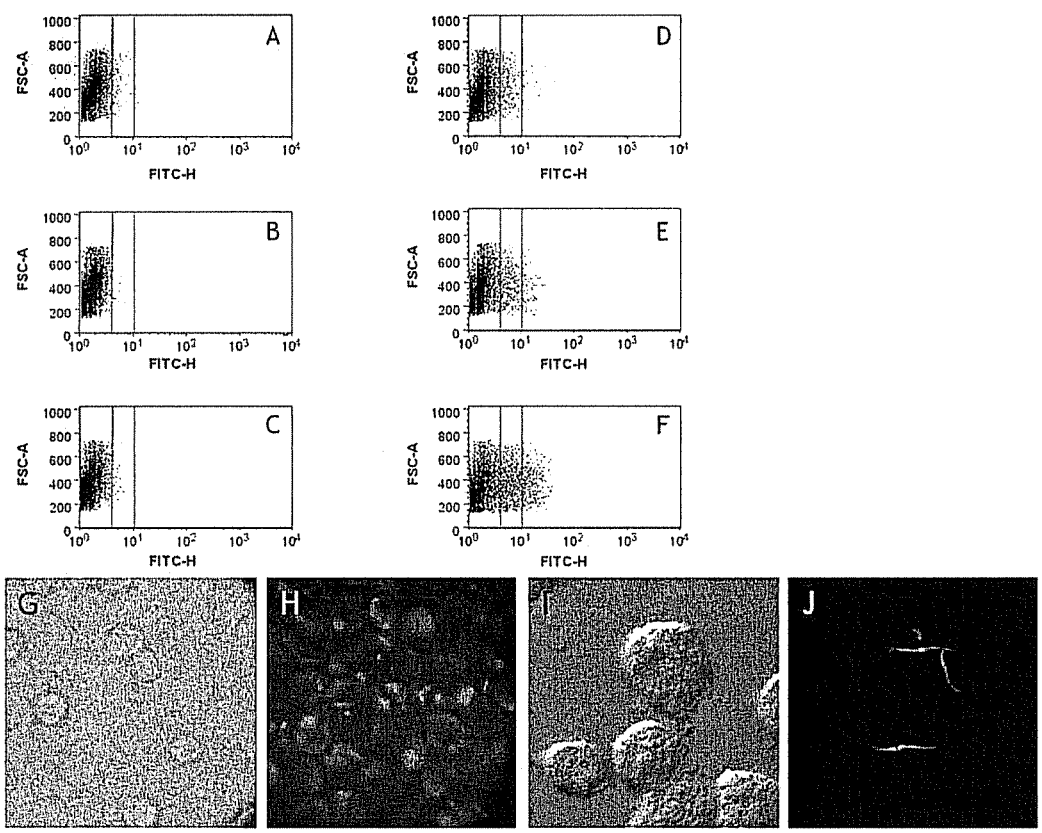
FIG. 12 is the results of FACS (A to F) and microscopic analysis (G to J) done using J774 cells infected with *M. smegmatis* containing Topo-pM90-EGFPh. The cells infected with *M. smegmatis* containing Topo-pM90-EGFPh (D, E, F) show more GFP fluorescence compared to the control cells infected with pM90-TOPO (A, B, C). The fluorescent (G, H) and confocal microscopic analysis (I, J) showed the same results. The number of cells used for the infection was 10 (A,D), 50 (B, E) and 100 (C, F) MOI (multiplicity of infection).
Figure 13A:
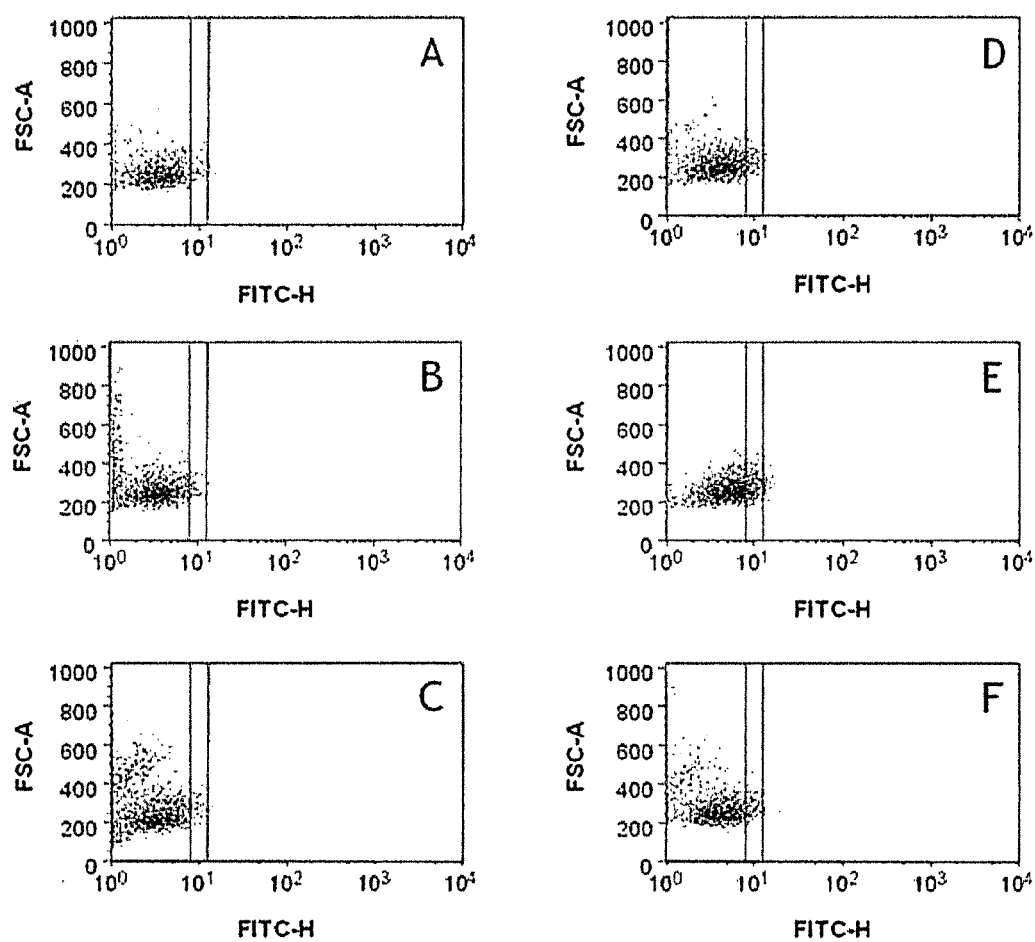
FIGS. 13a and 13b, each represents the results of FACS and microscopic analysis, respectively, done using J774 cells infected with *M. smegmatis* containing Topo-pM90-EGFPe. The cells infected with *M. smegmatis* containing Topo-pM90-EGFPe (D, E, F) show more GFP fluorescence compared to the control cells infected with pM90-TOPO; (A, B, C). The fluorescent (G, H) and confocal microscopic analysis (I, J, K, L) showed the same results. The number of cells used for the infection was 10 (A, D), 50 (B, E) and 100 (C, F) MOI.
Figure 13B:
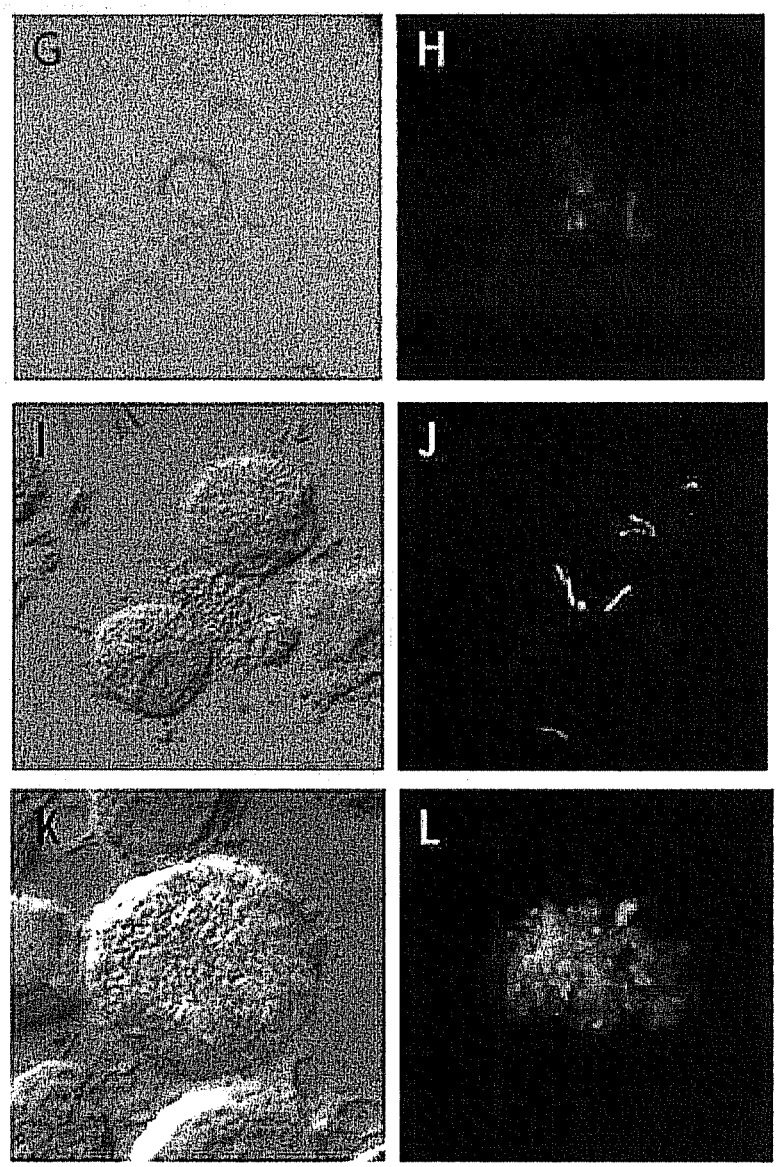
Figure 14:
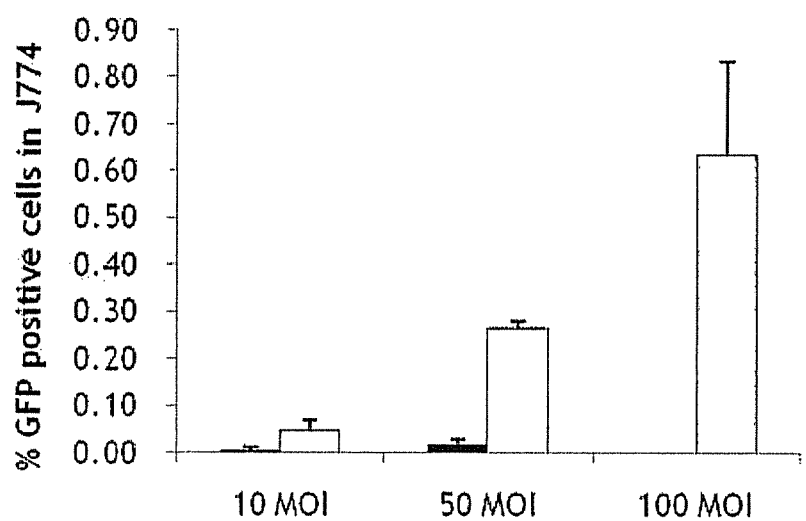
FIG. 14 is a graph showing GFP expression levels in J774 cells infected with different MOIs of *Mycobacteria* containing pM90-EGFPh (A) and pM90-EGFPe (B). The results indicate that the GFP expression level was excellent at all the MOI tested.
Figure 14:
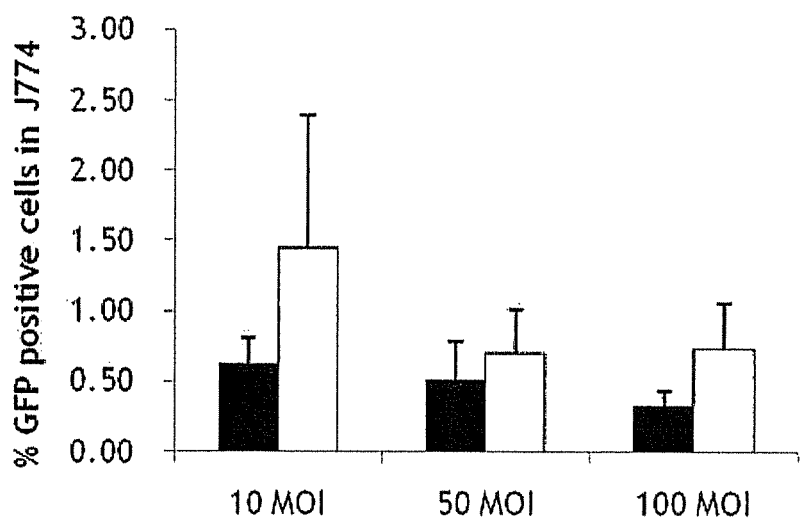

The results from the infection of J774 cells by Mycobacteria having pM90-EGFPh (FIG. 12) or pM90-EGFPe (FIG. 13) showed that the vectors of the present disclosure showed higher expression level of GFP in J774 cells compared to the control cells infected by pM90-TOPO. Also the results from the infection of J774 cells by Mycobacteria having pM90-EGFPh and pM90-EGFPe (FIGS. 14a and 14b) showed very high expression level of GFP at each MOI.

With respect to the use of substantially any plural and/or singular terms herein, those having skill in the art can translate from the plural to the singular and/or from the singular to the plural as is appropriate to the context and/or application.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

What is claimed is:

1. An isolated DNA molecule capable of replicating in a mycobacterium, wherein the DNA molecule comprises the nucleic acid sequence of SEQ ID NO: 1 and a transgene that is heterologous to mycobacteria.

2. A *Mycobacterium-Escherichia coli* shuttle vector comprising:
   (a) an origin of replication having the nucleic acid sequence as disclosed in SEQ ID NO: 2 (oriM);
   (b) an origin of replication for prokaryotic cells;
   (c) a promoter; and
   (d) a transgene, which is operatively linked to the promoter.

3. The shuttle vector according to claim 2, wherein the promoter is selected from the group consisting of a heat shock protein promoter, a CMV promoter, a promoter from a 65 kDa common antigen gene of mycobacteria, a ribosomal RNA promoter from *Mycobacteria*, a *Mycobacterium bovis* MPB70, MPB59, or MPB64 antigen promoter, a P1 promoter from bacteriophage Lambda, a tac promoter, a trp promoter, a lac promoter, a lacUV5 promoter, an lpp promoter, a $P_L^\lambda$ promoter, a $P_R^\lambda$ promoter, a rac5 promoter, a beta lactamase, a recA promoter, a SP6 promoter, a T7 promoter, a promoter from a kanamycin resistance gene of transposon Tn903 or Tn5, a metallothionine promoter, a growth hormone promoter, and a hybrid promoter between a eukaryotic promoter and a prokaryotic promoter.

4. The shuttle vector according to claim 2, wherein the transgene encodes a protein, antisense oligonucleotide, siRNA, shRNA, miRNA or piRNA.

5. The shuttle vector according to claim 4, wherein the protein is a reporter protein, an antigen or a therapeutic protein.

6. The shuttle vector according to claim 5, wherein the protein is a reporter protein selected from the group consisting of a fluorescent protein, beta-galactosidase, chloramphenicol acetyltransferase, human growth hormone, urease, and alkaline phosphatase.

7. The shuttle vector according to claim 6, wherein the fluorescent protein is selected from the group consisting of GFP (green fluorescent protein), RFP (red fluorescent protein), CFP (cyan fluorescent protein), YFP (yellow fluorescent protein), BFP (blue fluorescent protein) and their variants.

8. The shuttle vector according to claim 5, wherein the antigen is an antigen derived from virulent pathogens.

9. The shuttle vector according to claim 8, wherein the antigen is selected from the group consisting of a hepatitis B virus (HBV) surface antigen, a HBV core antigen, a human immune-deficiency (HIV) gag protein, and *Mycobacterium tuberculosis* Antigen 85A.

10. The shuttle vector according to claim 5, wherein the therapeutic protein is IL-12 or GM-CSF.

11. The shuttle vector according to claim 2, wherein the vector further includes one or more selective markers.

12. The shuttle vector according to claim 11, wherein the markers are selected from genes conferring resistance to an antibiotic selected from the group consisting of kanamycin, hygromycin, ampicillin, streptomycin, penicillin, chloramphenicol, gentamicin, carbenicillin, geneticin, neomycin, and tetracycline.

13. A cell transformed with the vector according to claim 2.

14. The cell according to claim 13 wherein the cell is a *Mycobacterium* or an *Escherichia coli*.

15. The cell according to claim 14 wherein the *Mycobacterium* is selected from the group consisting of *M. smegmatis, M. bovis*-BCG, *M. avium, M. phlei, M. fortuitum, M. lufu, M. partuberculosis, M. habana, M. scrofulaceum*, and *M. intracellulare*.

16. A method of using a first and a second vector for expression of transgenes in a eukaryotic cell, wherein the first vector is the vector according to claim 2, and the second vector encodes a transgene and comprises a pSE100 replication origin, the method comprising transfecting the eukaryotic cell with each of the first and second vectors.

17. The method of claim 16 wherein each transgene encodes a protein, antisense oligonucleotide, siRNA, shRNA, miRNA, or piRNA, and the transgenes encoded by the first and second vectors are different.

18. The method of claim 17 wherein at least one of said transgenes encodes a protein selected from the group consisting of a reporter protein, an antigen, and a therapeutic protein.

19. The method of claim 18 wherein:
the reporter protein is selected from the group consisting of a fluorescent protein, beta-galactosidase, chloramphenicol acetyltransferase, human growth hormone, urease and alkaline phosphatase;
the antigen is derived from virulent pathogens; and
the therapeutic protein is IL-12 or GM-CSF.

* * * * *

SEQUENCE LISTING

```
<160> NUMBER OF SEQ ID NOS: 38

<210> SEQ ID NO 1
<211> LENGTH: 18089
<212> TYPE: DNA
<213> ORGANISM: Mycobacterium intracellulare

<400> SEQUENCE: 1
cttcgccggg agctggggcc aggctgcgcc tggcaaacct tgacgagcgc ctgcggcgct      60
cttatgtgga ttctcaatca tgttgtgttt caacagtttt cgtgttgtcg cctatcggtt     120
gggccatgcc caaccagttg gtatgaactg aattatgtta taaatcaacg tttttcatcg     180
ctacccacat cgctacggct gcgccttcgc tgctaaatct tgaaacttgt ttattatcaa     240
```

```
catctttcac tgattatagc accgttcggc tacgccgcac tacctttata gctaactcaa    300
tttgctgcgt cacaatgttt gctagaactg tctcacagtt ggcataacca gaaccacaga    360
tacccgtgca accacatgca catgtccaca cccacacagt tgtgtacaca ctgtgctaca    420
cccaccggcc tacggccggt caccccatcc gagacgcaaa ccgcccatgc gcagcctgcg    480
ccgacacacc caacacggca ccaacagccg cccacgacgc accccgccga cgcgcatccg    540
ccaccgcaga caccgggtcc atcaccgcgc cacgatgcg caccaccaac aacgcccacc      600
gctgctcaaa cggggccagg cgctcccacg tcggatcggc ctcgtttcgg cccatcagca    660
gcttgacgag agccgccggc cgaccgactc ccacggccgg cccttcgcc agccgagctg      720 ccgcggtcag tcgcgccgcc tccaacccgg ctgccgccgc gtcagcagtc gccgccgcca    780
gctcatcact cgtcagctcg tcaaacacgg acttaaccct acattccgaa cccgacacca    840
tggcataaag actgacttga tattaatatc aagtcagtct ttatagatcg gagtgttcag    900
tggacgttct agacgcgctc accacgcagg ctcacacgct tctgacctgc gataaccgca    960
gcacaagccg atccccgtcc gtacagctcg cgcgatcggt gcacgccacg ccgccagcaa   1020
tcccggccga tgtgcgctcg catctgcggg gcgcgccgca cgttctgccg gcgcttgccc   1080
gccacgcaca ggcggcgac cggtacgcgc tgctgatcgc cgccgtgttc ctgcgcgatc     1140
tgctgcgcac gatcgccctg cgcgccgccg gcctccgtgg tgacgacatc gccgaacgca   1200
ccgacgacgc tctggccctg gtgtttacgc ttctacgctc cgctgccgag cccgacacgc   1260
ttaccgagcc actgatagcc gcacagctct ccaagcagct ccagcgccgc cacagcggcc   1320
cggacgccgc cgttctggtc gatcctcacg ccccgtact ggaccggccc agcagcgacc     1380
tggatcagga ccgcgacgcc gcccggcagc tcctcgcaga cgcccgcgac caccacgtca   1440
tcaccgcgtt ggagtaccag acccttgccg tgctctatct ccagcgcccc ggcaccctgc   1500
acgccaccca cagcgccgtc gaacgccgcg cccaacgcgc catccgcaaa ctcgcaaccc   1560
gctaccggcc ccatcacccc gtagccgcat aggacaacgc acgtgacgac cgcgcgggcg   1620
aatgaaatcc ctacgtgtca gacccaacac ctaaggtcca cccacatgac cgatgtcgag   1680
ctcagcgcct accggttcgc gctcgacacc actcctgccc aactcacgat gctgcgccag   1740
cacgccggcg ccgcccgatg ggcctacaac cacgcattgg gtgtgaagtt cgccgcactg   1800
gacgaacgca aaaccgtgat cgctgggctg gtggaacagg gccttgaccc gaaaacctct   1860
gcggcccaag ctccgaagat tccgacgaag ccagcaattc agaaagcact caacaccacc   1920
aagggtgatg accggatcag cgcggccggg gactgcccgt ggtggcacac cgtcagcacc   1980
tacgcattcc agtccgcgtt cgccgacgct gacaccgcgt ggaagaactg gctagcgtca   2040
ctgactggga aacgctccgg ccccataggg gcaccgcgct tcaaatccaa acatcgctcc   2100
cgtgattcgt tccgcatcca ccacgacgtc aacaatccga ccatccgccc ggatgacggg   2160
tatcgccgaa tcatcgtgcc ccgcttagga tcactgcggg ttcacgactc gaccaaacgc   2220
cttaaacgag ccatcgaccg cggcgctgtc atccagtccg tcacgatcag ccgcggtggt   2280
catcgctggt acgccagcat ccttgtcaaa gctccagccg cacatgcggc ccccactcgg   2340
cgtcagcgcc aggccggcac tgtcggcgtt gacctgggcg tgcatcacct cgccgccctg   2400
tccaccggcg acatcatcga caacccccgc cacttggctg ccggtcaaaa gcgcctcacc   2460
aaggcgcagc gcgcactgtc ccgcaccgag aaaggctcga accgccggcg gcgagctgcc   2520
gcccgcgtcg gccgacgcca ccacgaaatc accgaacggc gcgcgaccac cctgcacacc   2580
ctgaccaagc acctggccac caattgggcc accgtcgcga tcgaagacct caacgttgcg   2640
```

```
ggcatgaccc gatccgcccg cggcaccatc gacaaccccg gcacgaacgt gcgcgccaaa    2700
gccggacttt cgcgcgccat cctcgacacc tcaccgggcg agctgcgccg ccagctcacc    2760
tacaaaaccg gctggtatgg ctccactctc gcgatctgcg ataggtggtt cccgtccagc    2820
cagcagtgtt gcgaatgcaa agtgagaacc aagcttcggc tttcgcaacg cgtgttcacc    2880
tgcccagcgt gtgggtacgg accgatcgat cgggacgtgc acgctgcgcg gaacatcgcc    2940
gcctatgcgg ccgtcgcctc cgacaccggg gagacgttaa ccgcccgccg agataccgcg    3000
gaagccccca cacgtgtggg tcgccgccgc ggtgccgttg acgcgggaag accacaccgg    3060
gaaaccggtg cggccacccc agcagagcaa cctgctggtc acccaaagca cgcagatcag    3120
cgcacattac cgctggtcag ctagtgcgca ccccacgcgc gcacaggtga gtccgttgtc    3180
attgctgctc atcggccaat tcctccgcgc accccacgcg cgcacaggtg agtccgacca    3240
caaaccgctg gacgccttcg gtacgtcgcg caccccacgc gcgcacaggt gagtccgagg    3300
cccgtgaagc cgcgtggaaa ccgaatgcgc gcaccccgcg cacaggtgag tccggagctg    3360
cccccgacgc gcggcaccgc tgccagggcg cacccacgcg cgcacaggtg agtccaagcc    3420
cgagcagtgg aacacctcgg ccaggctgcg caccccacg cgcatgcact ggcccctaat    3480
cgccgccccg gttgctttgt acgggccgct ccgagccgca actgaggttg gcgcgctatg    3540
cggcctctga cagcgcgtgc cgggacgagt ccggccctgc cggcggtgag gcgtcgccgc    3600
gggtggctcg gtagagccgc atccgccgcg ccagtcggtc cccgcctcgg ctcccattgt    3660
cggcgtaggc cggttctccg ccggggcac tgctgcgccg ccaccgctg accggtgccg    3720
ggtcgccgtc aaggtaggtc gcgcctgaat ctggctcacc gccgccacca ccagacgggc    3780
cacccgacga cgcaccagcg ccgccaccgc cagacggtcc acctccacca ccgcctgacg    3840
gaccgccacc ggacggacca ccgccaccgc tcgcgctcgc tgaatctgat tcactgtcaa    3900
tgcgcggcgg cgggtttcgt ggattgtcgc cgtcatcgtc gtcgggtttc ggcttgcgcc    3960
gtaagtcatt tcgcagcctc gacacgtccg cggcccgctg caacagacca cgcccgccgc    4020
cagacgccgc gccaccgccg ccagacagct tggcggccat cgtgtcgcgc tgccgatcga    4080
acatccgccg cagcggcccg aagaacgcga accgaacgc cagcaccagg gcggtcagga    4140
acatcgcctt gatgacgttg ccgccggagt ccgcatagac gcggtccagc acgacgttgt    4200
aggccccgaa agccgcggtg tagacgacca tcgccgcgaa cgccatcaag cagtccagca    4260
ccgtcttgag cgcgaatgtc tgcgggccac cagggatcac acccaccgcg aacgcggccg    4320
gcggcatcta caacatggcc atgggcctgt gcctggccaa cggcaaagaa tgggactggg    4380
agaagcccga cgccgacccc aagcaccacg ccgactacct ggtcatcgcg tgctcggttc    4440
tcaccgacat ggttggcccg aacggcgtcg tccgcgacat caccgacatg gaagccgcca    4500
acggcccgct catgggcgta ttccggcccc gcaaatggcc cagcgaagcc atccccggag    4560
ccgtgcccat cggcgaagtc gcatagacga ctccaccagt ctgctggcat gactacccga    4620
tcattccggc acctgatcgg ctccctgtgc atcgtcggtc tcggctgtct gtttgacgcg    4680
ctggtagtgc tcccttagca gctcgtcgcg gttggtgctg gtgccctcgg cgcgggcctc    4740
ggcgcgcagt ttccggcggc gcgcgtcggc gttcttcacg ctgtaggcca gcagctcggt    4800
cagggcggcg tcggacagcc ccgccagttc gtcaatgtgc atggctggta ggtcgaactc    4860
gatgagctga tcgaccaccg cggtttcgtc gtcaacgaac agcccgcaca ccgggccgcg    4920
ggacaccatc gcctcgatgt agtggtcgcg cttgtgttcg gcggggcgac ggccttcacc    4980
gccgctgacg tagatccatt cggcgcggcc cggtaggtac tggcgcaccc accggctcac    5040
```

```
catgccgcca ttccacggcg gtcgggtcgt ggagatcgca taccgccatc ccagccggta    5100
cagcgcattg gccaactcga tcccggccgg catcggcgcg gcctgcgggg tatgcgcgaa    5160
gaaccggcgc cactgctcgt gtgtccgcgg ccccatcaac tcgcgctgat acgggcgcat    5220
gtcgcacagc agcccgtcga agtcgagcaa cgccaggtag cggcggcggt actccgggtc    5280
aggcgctccc ggccgcttgc ccttgccgcc cttcggcgcg cgtttgggtc ggctcggctt    5340
gtccaccgtg catttatgcc acggccgcgt tcggttctag cggagcaccc gccaaccggg    5400
aggcataaag caaatccgcg caccectcgg cggtcgtgct gtggcgcagg cacaggatca    5460
cctcggcggc ccgcgccgcc gccagcgctc gcactggtac agcccaccc tgcccggctg     5520
actgcatcgc cagcatgtac tcggtcagcg gcttgagcct cgcgttgttg acctcgcgcc    5580
acagcgcttc cgggaccggc ttccccagct cgtacaggtc catgacttcc tcgcatgcac    5640
cgctgctgag tcgtccggta ctcatcgcca tgtacatgtg ccgggaggcg atgcggtacc    5700
gctcctgttc gtcaaacctg ttggcttgct gccattccca cggcatcgcg accgcgcacc    5760
gatgcgccat cgccatatcc accccggccg gtttggtgat ggatttcggg tccacgtgca    5820
ccggccgcgc cgacacctcg gcggcgtagt cagtcacctg atccatgggc agtgacgacg    5880
ctaccgccag caccccggcta ccgggtgcgg ccatctcgcg ctcctgtgcc tgacgcacca    5940
cggtggcaag ggggttcgcc ccgccggcac tcgcggacga ctcccacagc tcgcggccga    6000
tcacagggtc ggtgaccgac agccgcacat ccggcggaat ccgcacaccc agcgggatat    6060
aggacgctcc ctcactggtg gccatccacg ccgccaccgt gccgcccgc tcgtacacca     6120
gcgccaccgc gtaatgaatc gtgatatggc cggcccacac ggtctgggcc accatcgccg    6180
acaccacgtc gcggcccaca tccatcgcct gcccgaacag cacatcgccg gttgcgccgt    6240
ccgcgccgac accacgcaca cccggcgtcg tgtgcaacgg gaccggggcc agagacgaac    6300
ccgccgcggc cggggtcgca ccgcccacac tcgataccgg tgtcgcagcc gcggccggcg    6360
tcgcagccgg cccaccacca accaccggac cgccgaccgg actgaccacc gcaggtccac    6420
cggcagcagc ggccggcatc atcccgattg gcgcaccgcc gaccggtgcg ccagaaaccg    6480
gcgctgatgc cgccgctggc ggcgcagcag ccggggccgc tggcgcggca gccgacgcgg    6540
ccgacgccgc gccctgggcc acctgagacc cgatattgcc cgccgcacca agggtgttcg    6600
cggtcgcgtt gaccgcgccc gacgccagcc gcgccgacga ctcagcgata ccagacccgg    6660
cactggccaa gcccgcacca cgcaacccg acgcgccgcc ttgcgcggca ccaggcgcac     6720
ccgcaccggc cggggaaccc ggcccgcccg cgtgcccagc ggccggggac gctgacgctg    6780
ggccaccacc tgacgacagc ccgctacccg acgaggcggg cgacgacgag gacgccgggg    6840
acggcgacat cgaccgtggc atcatctgcc cgatcatcga cgacccaccg cccgacgatg    6900
ccgacgaacc ccccgacgac ggagacgaca tcggcggcga cgaatgcgcc ggcgacggca    6960
acggccgatc cgggttagcc gccgcagcgt ctttcgggtc cagcgcattc ggcttccacg    7020
cagctttacg ggcctcgtta gatagcgacg gtttctcggc ctgtttcgcg tcccatgag    7080
cggcgtcggc gggcgaaccc tgtttcatcg tgttgtagtc gacggcctgc actccactgc    7140
cattggccgg tgaaagaggc ggcgaatagg ccccctcacc gcctatccct gtagagagcg    7200
gtgtagccgc gccggcccg ccactttgtt tggcgctgcc agacggcggc gaccacgaca    7260
gcagttcggt ggtcttggcg gtcacctcgg cggcgcgggc tgtgtccctg gcgagtgcct    7320
cggcttgggc agcttctatg atcgccgcta tctgcgctgg cagggtcgcc gcagcccaa     7380
taccgccttt gctttcgagg tctttgatcc tctgatccgc gctcatcacc acccagtaca    7440
```

```
gatcggattt gaggtccact attgacgccc gaatcgagtc ggccgcaggg ctcgcgacgg      7500
ccagcgcggc gatgcgatca gcgagcgtcc catcgcgctt tgcgaccatc tgattaatgg      7560
ccggaatcat gcccacggac gtctgcccat cgaggttctg tttgatgctc tgctgggcga      7620
actcttgatc tatcaatcga ccccattcgg ccttcaattg ctcggagtac gtccgccaca      7680
cgtactccga ttgctccggc cagtgcatgc ccttttcact gaccaaaatc aggtcagcgt      7740
atttcgacgg cgggtactcg atagcgctca tcggggagcc aaccgttcac acagaacatc      7800
catcgtgttc gccgacactt tgaggatgtc gtacgagttt ccacccgcgg catcgtaggt      7860
cgcatcagcg gtcgctaagg catggagtgc accggctgtt gaggtcgccg tctggtcaag      7920
aatggcggca gttccgggtg cgatgccaga ggccagtttg tcgccagcga gcttgtattg      7980
ctcggcggcg cgttgcaccg cagccgacca atccgggttc gcccgcactg tgggatcaag      8040
aatcttcgtt cctggcggca acgcggccaa ggctgtagcc gcatcgttga tcagggtgcc      8100
ggtcgatacc catgtgtcgc aggtctggcg gttagcctcg gctgcgggca acggggccgg      8160
tggtgtgggt gcggcgggca gtgtcgcggt gatcgttacc ggcgtccgcg cggaggtgtc      8220
gcgggtgccg gccatgaacc ccgccgtcgt cgccgcggcg acgacggcgc cgatcgccac      8280
gccaccaacg aacaccggcc agcgccggcg agctgccggc ggcggtagcg gtgccggcgg      8340
cgggtacggc gtcggtggcc cccagttggc cggcggtcgt gtggtttccg acatcagacc      8400
gtgaacacct ggccggttcc cggtgctagc ggcgtcaccg ccggtattgg aaggttacg       8460 gatcgctggt agtcgccggc tgcttgttgg tcttgctgca ccacggtcgg cggggactcg      8520
gtgagtgagg ccgtctgtgt gcccgctgcg gcggcgtcgg cggcgtcggc cttggcgatc      8580
atcgccacga tggcgttagc cgccgcgcct gcggcgatgt ccagcagtga tgtcccgccg      8640
ggtggcggcg ggaccaaagg ggctggcacg ctggcggttt ccgtagcacc ggccgtcgcc      8700
gcgcccgcgg ccagcctctc cggtgacacg ttcagagtgt tgtcagtgct gctcataggc      8760
caaatccctc cccgctcata ggtctaatcc tccccgaggt ttgcgacaca gggaacagct      8820
cgccagccta aacaatgcgt ttcccctggt cgcggccgaa gcgagggtat tctgcgagat      8880
tgtcgagcta cctaaaatcg gcctgtaaag gtggggccgc tcggcttcct cgactcgttc      8940
ctcgctcagc gccgagcgta cccccccttgt caaggttgac gggcaaattt gcaggtgggc      9000
gtgtttctgt atgcccacac gcacagaaac acaggtgtcc accaaccatg cccgcacggc      9060
caaattgacg cggctcagac cgacacaatc gcacatcgtt accgaatcgt tatcgtcaga      9120
ttgtcgtctg agccgttttc caactttctc gaaaattctc tctacctgca ccggcgtgtc      9180
ggcgtcctac gtatctgata gttcgcaagg gtgtcgggta tggctcaacc acacaagggt      9240
ccgcgtcgcc tggttcagtc gcgtatctcc gaagaggtct acgccgaagt gtccgcacgt      9300
gcgcgtgccg ctggcatgtc cgcgtcccaa tggatagccg acaacacagc gctggcggtt      9360
ggccggcccg atcttgtccg cgagctgaac cgcaccgagc gtgaggagct gccgctggcg      9420
atttgagaac cgcgcccgac gaaagaggcg ggcaacacga catctcaata gttggcacgg      9480
agctcctaaa cgacgacagc cccgctaatg cggggccgca acgtcgattt ggctctactt      9540
cgtctctgga gtttcgtctc tggagtttca ggtccgagcg gctaactcgg tcctaggcgt      9600
ctcccgtgcc gcgcccccga agggacagtc ttgctggact ggtctcacgg tagcgcatac      9660
ccgaatcaga ttcgtggtga cgcgcaaaac cgtgatctca catttacaga ttcccgtgca      9720
tccgtgtgca cggattcacg cccatctggg cattcacgtg gccgttttgg tgcctccgtc      9780
tgggctctcg tcgctcccgg cggcgcgtcg tggtgacaac cgcgttcgac gcggcagaga      9840
```

```
ttgccgccgc ggtcccggaa tctggctcac cgtgcagcgg tacagcgtca gctcgactgc   9900
gcagaatccg cgccaaggaa gcccgcaggg cgtcgatcga acgctgtggg gcggtgccgg   9960
ccgcggtgcc gatgtggtcg tcgcgggagt tgtggactgc cgatctgcgg gtgcttttgt  10020
cgggtccgga gttcagcacg cgccgggtga tttcggcggc gacggtgctc gctgtcgcgg  10080
tggcgatggc cgagttcgcc gaccatgcca cgggccgcaa tgtggcggtg acaaacgagg  10140
ttctggccga gcgcgcgagg tgttctaagc gttcggtgac cgcggcgcgc ggggtgttga  10200
aagcgttggg tgtcgcggtg gaagcggtac gtgggcatgg ctctgcgacc acacacacgg  10260
tcggtaatcg accgagcatt tggcacctgg taagccgacg ccagcccacc atcgacaacc  10320
cgcccacggc cccgcagaac ggccgcggcg agcctgccga tacggtgccc gatcgcggcc  10380
agagcgcgcc cgtggctgtg gagacttgcg acctaccacc atcccgtagg gataggtggg  10440
taactcctgt tgagaattac tcaccaagca cgcgcgagcg cgcgagcgcg gaaaattctt  10500
ccccaaaaca aacacaaccg gcgcggtcgc ggcggcgcta ccgcgccacg ccgcgcccccc  10560 tggacgttca gcgactcgcc gccggcctgg tcacgccggc agtcggccac ggcccagaca  10620
acgacgggcg gcgaaccgcg ctgatcgccg gcctggagca gggccatatc ggggccatct  10680
gcgacgcgat cacgacggcc ggcatcgacg cgaccgcctg gactccgaag acgctcacgg  10740
cggcactgaa cgccgacgcg cggggtgaccg gctggtcgtg gccggatcgc atcgaacgtc  10800
ctggcgcgtt cctggcgtcg cggctgcgcc gcctgcccgc acggcccgac accagtggcc  10860
cggttgacaa cggcctggat caggcccgta ggacacccgt tgagccgtca gcggcccgtg  10920
tagcgccggt acagacggcc gctggccgcg cgtacgcccg tgcgttgttc gccgagcagc  10980
gacggcaccg ggtgaccgcc gccaatgccc agtcagccgc ggtgccggtg cgccaaagtg  11040
cgccagaaac cgcggtgtgc gcaacgtgcg gatgctcgga cgcaccacgg cggcggttcc  11100
tgccaacgcg gcgggctcac atttgcgatg cctgtttcca aggatgtggt ggtgggcagg  11160
cgcgtactgg tcgcgtcgga acggtcggca gcagttccgc ggtgccacag tgccagtagt  11220
cgggcagggc ttgcacgggg atgcggaccc atccgccggc cgcggccggc gatgggtcca  11280
gtgtcgcgtt agggccgtcg tccagccgcg ccagctcgcg gtcggatgcg atcagcttgg  11340
caccgtagat gtcgtcgtgg cggcggtccc acgtgttggt gatgcggtcg cggtaccagc  11400
ctgtccagtc ttcgccggtg ccgccggcgg tgagcccggc ccggtaccac gcttcgaggc  11460
gatcacggcc ccgtgcgtgg ttgatggtct gggccgcagc ccagtccgcg tcacggaggg  11520
ctctgtcggc ttcgtccatg aacccgcgcc gggtcatgtc gatgatggct ggcgacgggg  11580
cgtcgtaggg gcctggcatg gcggaggca gtcggaactg ttgcggtttg cttgcgttca  11640
gttcctcgtc ctgctggtgg gtgcggtcgt gcagggcaag gctgtcgcgg taccaggcgt  11700
cgagcgcggt gcgccagtcc ccgccagtgg cgtagggctc ccacggttgc ggtggcaggg  11760
tggtgaactc gtgcaggacc aggccgtcga tgtcgtcgcg cagttcttca ccggcgatgg  11820
cggcgatgcg ggcgcagtag ccgggcagat ggctacgcca gtcggcgggc agttcgccgc  11880
tgcgcgccca ccgcagcaca tcggcccaca accgttacg cgaaccgata tacgaattgc  11940
ggtctcgcca ttcgctgtgc tcacgtgcgt actggtcgcg ggcctcggcg tcgcgctggt  12000
ccagctcagc ggcgtactgt tcgtagattt cgatctgaaa cccgtaattc ctagatgcct  12060
cggcgttgcc gttcagatcg gccaaccgct tgccgtcctg tgcccggcgc aagccatcgg  12120
tggtggtctg gcgcaggttg tccgacactt gccaggtcca ctcggggaac gcgcccgtgt  12180
gcggccagcg cggctgtggc tcacccatcc tgctgggtgg tgtcggcgta gtgggcttcg  12240
```

-continued

| | |
|---|---|
| aggagtgcgc gcacttcgtc gagcatcgtc acgccggtgg tggcggcgcg gatcttcatg | 12300 |
| gcgcggtgca ggcgttcggg gatgtcgagg gtgagccggc gggtgggttc gcgcggtggt | 12360 |
| ggtggtgtgg ggctggtggt cgtcacggtc gcagccggcg tcgcggtggt atccccgtgg | 12420 |
| acccatttat ccttgtcgat gacgctgggc cgctgggtga ggttgggtcg cttctcagcc | 12480 |
| atggttgatt gcctccaatt cggtggtgac tgcgcggatt tcgtcgtcag cgaccccgcc | 12540 |
| ggggtcggat tcgtacacgg ccagcccgag accgttggct tcggagtaga tgacccggtt | 12600 |
| ggcgacgtta gcctccagca ggcgtggccc atattcactg agctgctgtt tcacgtcacg | 12660 |
| ggcgatcttg gtgttaacga tgcgccggtt gatcacccac acggcgatca cgggcttata | 12720 |
| gatctgggat tgctcgagca gggtgagcac gtcggcgctg cccatatgt cgtacgcgct | 12780 |
| gggctgtacg gggatgacca cgacatcgga ggccatgatc acggcgcggg cgacggcttc | 12840 |
| gacgcggccg ggtgcgtcga tgatgatgtc gtcgtagccc tccccgagtt ggccgatttc | 12900 |
| tcggtggatg gtgtctcgcg ggaacccgac caccgacatc agcggcgggt gttccagccg | 12960 |
| gccgcgttgg gcctgccagt ccagcgccgt accttgctgg tcggcgtcga gcagcagtac | 13020 |
| gcgccggccg cggcgggctt tctcggcggc gacgttgacg ccagcgtgc ttttgccgac | 13080 |
| cccgcctttt tggttcacaa agctggtcac acgtggaggt gtcattgcgc cagtgtaacc | 13140 |
| acaaaggcag ccacatacac gggtaacatc atttgcgtgt tgtcgtgcac acgcaaaccc | 13200 |
| ggatatgcga gaatctttgt aatcgtgctt ctgtgtacac agaaagggca ggtggcggga | 13260 |
| tggatgagca cctgatcatc accggcgggc ggacgtaccg gatacctgcc ggcgacaacg | 13320 |
| aggacatgga cgcgcttctg gcgtggtggg tggagtcgcg gggcgaaccg gcgtcggtgg | 13380 |
| cagcgttgtc gcgtcagcag gtgttcgccc ggattcgccg ggcggcgatc ccggccgggt | 13440 |
| tcccggagcc cgatgtggtg atcggtgaca ccgaccgcga cagcggcggg tttgtccgcg | 13500 |
| gctggctgcc ggcgacggtg caggcatggc aagacgaaca agacaagccg gccgcttccg | 13560 |
| gcgcgcccac cgagccggcc gcggccggtg agccggtcgg ccaggacgaa cccgcgccgg | 13620 |
| ctgatcccgg cccggccgct ggtgacgatg aggacgtgtg gcggatgggt gcacgccggt | 13680 |
| ggaccggtgt gggcgatcgg gccgacaagt tcgtgcgcat cctgacgagc gcggcgcgc | 13740 |
| tcaccccgtc cggggtggtg tcggcgcggg taccgctgga tgccgcattg ctgggccagt | 13800 |
| acgtgtggaa gcactggccg cagaaaccgg cgcagacacc acagctgtgg gtgacagcgc | 13860 |
| cggcgttggc ggcggcgggg atgagcccgc cgaagcggcc cccgacgacc tcggaggact | 13920 |
| tgtccgacgc ggtggccaag gcgttcggtt gtgaagtcac cgcggcgacg gccggatggt | 13980 |
| tcaccgcgca gttccgcgat cccgcgggtg gcgtggaggc gcgccgggta catctggtgc | 14040 |
| tgctgccgtt ccgctggttg gacccggcgt cgcagcggcc caacgatgag ggcatggccg | 14100 |
| gcactcgcgg cgctgcgtcc gagctgcccg acgacgagga caacgaggac gccgcggtgg | 14160 |
| cggtgctggg tgagcgcatc gcgtggctgg cggcgctggc cgacaagacc gacagccacc | 14220 |
| gccgggagct gccggtggtg ccggcggcgc ggccggcaac ggtcggggcg gcgctgctgg | 14280 |
| acgtggtacg caaacgtgaa cgcaaaccgc accggttgga ggcgttcccg gtgcccgaca | 14340 |
| ccgtggccgc tgaaacacca cgcctggacc ccgatttgga gaactggaag aacatgccgc | 14400 |
| acaccgccaa aggtgatgcg gtcgatgtcg aggttgatca gcgggcagcg ttttggcca | 14460 |
| gcacagggca ggtggaattg ggatatggcc ggcggtgga gatgcccaag gtggacgccg | 14520 |
| cggtgttcgc cgacaaaccg ccgttcgggc tgtggcgggt gaccacgccg ccagcggcat | 14580 |
| cgttggacgg cctgagccgc cgcctgccgc tgccgcacga atacatggca tgggaggccc | 14640 |

```
cggcgacgtt ttgggcgacg acacgggccg ttcagcactt gctggcgccg gtggacgacg   14700
gcggcgcggg ggtgtcgatc ggtgagttgg cgatcgacgg ggcatgggtg tggccggggc   14760
atgcccggct gctgcgcaac tgggcggacc tgctgcggga tcggctggcc gcggcgctgg   14820
cggatggcga ccagttccag acggacatgc tcaaaaacat ctacaaggcg tttctggggc   14880
ggatggctgg tagccagcac ccaccggggc agcggcacta ccagcaaccg gtgtgggtgg   14940
ccacaatcca cgcggacacc cgctggcggg ccatgcgcta cgccaccgcc accgcggcca   15000
cgcacggtct gtatccgatc gcggcccgcg acatcgacac gttcgtctac cggattccgg   15060
cggacatgga ccccgcggtg ctgagtgaag aatcgaccgc caacggtaag taccgggtca   15120
aaaaggtcag gaccggtgac cactgatggc gcgctggggg atgcccgaac cgcgcgaggt   15180
cccgccgccc gccggcctg cggctgcggg tgcgccggca gcggcccccc cggtgcgctc   15240
acgcgggttc ggtgcggcgt tcaaggcgtt ggtgggccgc aagctgaacg agctgcgggg   15300
ccggcattgg cggcaggtcg ccgaacaggc cgaacagggc agccgcggtg cgcagcgggc   15360
aatggaggct gaggccgcgc ggcgcgctgc cgcggagatg gcgcgccgga tcgaacgcca   15420
gaccgggcac cgcccggccg aggccaccat ccggcgcaat gcccgccagg accgcactcc   15480
gaagggtgcc gatcagaccc ggatcgaccg acagtcccgc attgacaccg ccggcggtat   15540
tgaccagttc gcccgccagg tggggccaa cccgcgagct gtgccgcaat ggcgcgacgc   15600
cggcgcgagc ctcgtcggag acggggtgcg ggtgtcggcc gacgtggagg gcatcctgtg   15660
ggccgatggc gagggatacc cgcgggcgat gacggtcagc gtcacgatca gcgatcctga   15720
cgtggccgac gagctccgcg ccgccaacgc cgcctgggac ctcgaagcgg tcgccgaaat   15780
gctggggccg gtgatcaccg cacaaaccga ttgggccggc gcggccgaac gccggtatga   15840
ggtggaggtc atcaccgaca tcacggtcat ctgagatttc cggggactca tccggtcatt   15900
ccgaggaaga cgagtaggcc gcgttcgagc tggagcattt cggtggtcga taccttgccg   15960
atgcgctggc cgatcttgga cctgggaacc gtggtgattt tgtcgatcat gatgtggctc   16020
ggtgttgtga gtccgttgga ggcgttgggc tgcacgggta ttcgcagcag gggtgcaccc   16080
gtggtgtttt ttgtgagggg gcagattgtg acggaatctg tggcgtcgaa acggtcgtcc   16140
tggacgacga gcaccggccg tggtttgccg gcgtagtcgc ggccggaggc cgtccaaagt   16200
tctccgcgca tcactgggcg tcgaagtcct catcgttgaa cgcggagatg gcatccacaa   16260
acgcctggtc gtcggccgcg ctgtcggagg cggctacgag ggccgactgg cggtgagctt   16320
cggcggcgaa tcctggtgcg cgcgtgtcgg gtacccatat ttgaagggg cgtagccctt   16380 gctcgcggag gcgggttcgg tggtcggcta cgcgcctgtt gatgtcccgg ttggccatac   16440
acgcaatgtt acatgtaact ttgtgggctg tgggcaaccg ctgattctca gcgcgcctgt   16500
ggcgcttgga gggaagaccg gacaggaagg ggccagcggt gacgacaccg acgccgaaga   16560
agggatcgac ggacgcggtg aaagcggctg ccgtcaaaaa ggctgccgct cgcgcggctg   16620
cggcgtcgac ggagctggag aaccgggccg tgccggccgg ccacgtccgc tcccgtggca   16680
ccaaggctct cctggccgag cggcaagccc gcaagcgctg atgccagagt gcccggccga   16740
tgttgtgcac atcagccggg cacgtcgggg ccgttacgcg gcgatttcgc cgagaggcac   16800
ggctccgggg atgatctcgc tgggccactt gcggggccgg aaccagccca ttggcgggcc   16860
gctggtggct tccatgtcgg tgatgtcccg gacgacgccg ttcgggccga ccatgtcggt   16920
gagcaccgag cacgcgagga ccaggagtc gatatgggt tgcggatcgg cgtcgggcag   16980
ttcccagttc cactctttgc cgttggccag gcacaggccc atggccatgt tgtagatcgc   17040
```

-continued

```
gccggcgatc agcgggtgag tcttggcggc ggggtagtgc tgctcgatca gggcgcggtc    17100
gatttcggtg acatcgggtt tgtcgggtag ctcgatgtcg tcggggtggt acgggttgcc    17160
gacgcggctc atttcgcaga gtgctttggt gggccacggg tcgcgcgggt accagccgcc    17220
ttccatgtag gccctgacag aggtgtgttt tccttctacg tgcacgagat accagtgccc    17280
gacttggagt tgcggtttca tgttgcggag acccttccg gtaggtgaat tcccaccgt     17340 ggttttcacg ctagccgcc gggccgacaa ggtttccgac acgccgcggc gttctggggt     17400
tgtggggccg ggccgggcca ggcttaccgc tggggtcgtt ctgtgtcgcc tatgcggccg    17460
gcgtcgtcgc ggccacgctc aaccatgtcc agcatggctt gccggtagcc cggcgacgtt    17520
ggcctggtgt agaggccagc ccgtttgatc tgagccagcg tgatgccgcg gcggtgctcg    17580
tcttcacgat cgccagaggt catgcgtcga ttgtccctcg gccgcgtgcg catgagcggt    17640
ttgcgtctcg gttggtgtga tgggtggccg gcgggtgtaa cccggcggtg gtgtggtggg    17700
tgtggacatg tgcatgtggg tgcacgggta tctgtgtttc cggttatgcc aactgtgaga    17760
cagtgctagc aaacgttctg atatagcaaa gtgagttagc tgcaagagta gtgcggcgta    17820
gccgaacggt gctataatca gtgaaagaca ttgataataa acaagtttca agaattagca    17880
gcgaaggcgt agccgtagcg gtgggagata agatgaaaac tgttgatata caacataatt    17940
cagcttatac caactggttg ggcatggccc aaccgatagg tgacaacacg aaaactgttg    18000
aaacacaaca gaattgataa tcacataaga gcgccgcagg cgctcgacaa ggtttgccag    18060
gcgcagcctg gccccagctc ccggcgaag                                     18089
```

```
<210> SEQ ID NO 2
<211> LENGTH: 2469
<212> TYPE: DNA
<213> ORGANISM: Mycobacterium intracellulare

<400> SEQUENCE: 2
```

```
aggcgggcaa cacgacatct caatagttgg cacggagctc ctaaacgacg acagccccgc      60
taatgcgggg ccgcaacgtc gatttggctc tacttcgtct ctggagtttc gtctctggag     120
tttcaggtcc gagcggctaa ctcggtccta ggcgtctccc gtgccgcgcc cccgaaggga     180
cagtcttgct ggactggtct cacggtagcg catacccgaa tcagattcgt ggtgacgcgc     240
aaaaccgtga tctcacattt acagattccc gtgcatccgt gtgcacggat tcacgcccat     300
ctgggcattc acgtggccgt tttggtgcct ccgtctgggc tctcgtcgct cccggcggcg     360
cgtcgtggtg acaaccgcgt tcgacgcggc agagattgcc gccgcggtcc cggaatctgg     420
ctcaccgtgc agcggtacag cgtcagctcg actgcgcaga atccgcgcca aggaagcccg     480
cagggcgtcg atcgaacgct gtgggcggt gccggccgcg tgccgatgt ggtcgtcgcg      540 ggagttgtgg actgccgatc tgcgggtgct tttgtcgggt ccggagttca gcacgcgccg    600
ggtgatttcg gcgcgacgg tgctcgctgt gcggtggcg atggccgagt cgccgacca      660 tgccacgggc cgcaatgtgg cggtgacaaa cgaggttctg gccgagcgcg cgaggtgttc    720
taagcgttcg gtgaccgcgg cgcgcggggt gttgaaagcg ttgggtgtcg cggtggaagc    780
ggtacgtggg catggctctg cgaccacaca acggtcggt aatcgaccga gcatttggca    840
cctggtaagc cgacgccagc ccaccatcga caacccgccc acggccccgc agaacggccg    900
cggcgagcct gccgatacgg tgcccgatcg cggccagagc gcgccgtgg ctgtggagac     960 ttgcgaccta ccaccatccc gtagggatag gtgggtaact cctgttgaga attactcacc    1020
aagcacgcgc gagcgcgcga gcgcggaaaa ttcttcccca aaacaaacac aaccggcgcg    1080
```

```
gtcgcggcgg cgctaccgcg ccacgccgcg cccctggac gttcagcgac tcgccgccgg      1140
cctggtcacg ccggcagtcg gccacggccc agacaacgac gggcggcgaa ccgcgctgat      1200
cgccggcctg gagcagggcc atatcggggc catctgcgac gcgatcacga cggccggcat      1260
cgacgcgacc gcctggactc gaagacgct cacggcggca ctgaacgccg acgcgcgggt      1320
gaccggctgg tcgtggccgg atcgcatcga acgtcctggc gcgttcctgg cgtcgcggct      1380
gcgccgcctg cccgcacggc ccgacaccag tggcccggtt gacaacggcc tggatcaggc      1440
ccgtaggaca cccgttgagc cgtcagcggc ccgtgtagcg ccggtacaga cggccgctgg      1500
ccgcgcgtac gcccgtgcgt tgttcgccga gcagcgacgg caccgggtga ccgccgccaa      1560
tgcccagtca gccgcggtgc cggtgcgcca aagtgcgcca gaaaccgcgg tgtgcgcaac      1620
gtgcggatgc tcggacgcac cacgcgcgcg gttcctgcca acgcggcggg ctcacatttg      1680
cgatgcctgt ttccaaggat gtggtggtgg gcaggcgcgt actggtcgcg tcggaacggt      1740
cggcagcagt tccgcggtgc cacagtgcca gtagtcgggc agggcttgca cggggatgcg      1800
gacccatccg ccggccgcgg ccggcgatgg gtccagtgtc gcgttagggc cgtcgtccag      1860
ccgcgccagc tcgcggtcgg atgcgatcag cttggcaccg tagatgtcgt cgtggcggcg      1920
gtcccacgtg ttggtgatgc ggtcgcggta ccagcctgtc cagtcttcgc cggtgccgcc      1980
ggcggtgagc ccggcccggt accacgcttc gaggcgatca cggccccgtg cgtggttgat      2040
ggtctgggcc gcagcccagt ccgcgtcacg gagggctctg tcggcttcgt ccatgaaccc      2100
gcgccgggtc atgtcgatga tggctggcga cggggcgtcg taggggcctg gcatgggcgg      2160
aggcagtcgg aactgttgcg gtttgcttgc gttcagttcc tcgtcctgct ggtgggtgcg      2220
gtcgtgcagg gcaaggctgt cgcggtacca ggcgtcgagc gcggtgcgcc agtccccgcc      2280
agtggcgtag ggctcccacg gttgcggtgg cagggtggtg aactcgtgca ggaccaggcc      2340
gtcgatgtcg tcgcgcagtt cttcaccggc gatggcggcg atgcgggcgc agtagccggg      2400
cagatggcta cgccagtcgg cgggcagttc gccgctgcgc gcccaccgca gcacatcggc      2460
ccacaaccc                                                             2469

<210> SEQ ID NO 3
<211> LENGTH: 399
<212> TYPE: DNA
<213> ORGANISM: Mycobacterium intracellulare

<400> SEQUENCE: 3
atggtgtcgg gttcggaatg tagggttaag tccgtgtttg acgagctgac gagtgatgag       60
ctggcggcgg cgactgctga cgcggcggca gccgggttgg aggcggcgcg actgaccgcg      120
gcagctcggc tggcgaaagg gccggccgtg ggagtcggtc ggccggcggc tctcgtcaag      180
ctgctgatgg gccgaaacga ggccgatccg acgtgggagc gcctggcccc gtttgagcag      240
cggtgggcgt tgttggtggt gcgcatcgtg ggcgcggtga tggacccggt gtctgcggtg      300
gcggatgcgc gtcggcgggg tgcgtcgtgg cggctgttg tgccgtgtt gggtgtgtcg      360 gcgcaggctg cgcatgggcg gtttgcgtct cggatgggg                            399

<210> SEQ ID NO 4
<211> LENGTH: 1476
<212> TYPE: DNA
<213> ORGANISM: Mycobacterium intracellulare
```

<400> SEQUENCE: 4

```
atgaccgatg tcgagctcag cgcctaccgg ttcgcgctcg acaccactcc tgcccaactc      60
acgatgctgc gccagcacgc cggcgccgcc cgatgggcct acaaccacgc attgggtgtg     120
aagttcgccg cactggacga acgcaaaacc gtgatcgctg ggctggtgga acagggcctt     180
gacccgaaaa cctctgcggc ccaagctccg aagattccga cgaagccagc aattcagaaa     240
gcactcaaca ccaccaaggg tgatgaccgg atcagcgcgg ccggggactg cccgtggtgg     300
cacaccgtca gcacctacgc attccagtcc gcgttcgccg acgctgacac cgcgtggaag     360
aactggctag cgtcactgac tgggaaacgc tccggcccca taggggcacc gcgcttcaaa     420
tccaaacatc gctcccgtga ttcgttccgc atccaccacg acgtcaacaa tccgaccatc     480
cgcccggatg acgggtatcg ccgaatcatc gtgccccgct taggatcact gcgggttcac     540
gactcgacca aacgccttaa acgagccatc gaccgcggcg ctgtcatcca gtccgtcacg     600
atcagccgcg gtggtcatcg ctggtacgcc agcatccttg tcaaagctcc agccgcacat     660
gcggcccca ctcggcgtca gcgccaggcc ggcactgtcg gcgttgacct gggcgtgcat      720
cacctcgccg ccctgtccac cggcgacatc atcgacaacc cccgccactt ggctgccggt     780
caaaagcgcc tcaccaaggc gcagcgcgca ctgtcccgca ccgagaaagg ctcgaaccgc     840
cggcggcgag ctgccgcccg cgtcggccga cgccaccacg aaatcaccga acggcgcgcg     900
accaccctgc acccctgac caagcacctg ccaccaatt gggccaccgt cgcgatcgaa       960
gacctcaacg ttgcgggcat gacccgatcc gcccgcggca ccatcgacaa ccccggcacg    1020
aacgtgcgcg ccaaagccgg actttcgcgc gccatcctcg cacctcaccc gggcgagctg    1080
cgccgccagc tcacctacaa aaccggctgg tatggctcca ctctcgcgat ctgcgatagg    1140
tggttcccgt ccagccagca gtgttgcgaa tgcaaagtga gaaccaagct tcggctttcg    1200
caacgcgtgt tcacctgccc agcgtgtggg tacggaccga tcgatcggga cgtgcacgct    1260
gcgcggaaca tcgccgccta tgcggccgtc gcctccgaca ccggggagac gttaaccgcc    1320
cgccgagata ccgcggaagc ccccacacgt gtgggtcgcc gccgcggtgc cgttgacgcg    1380
ggaagaccac accgggaaac cggtgcggcc accccagcag agcaacctgc tggtcaccca    1440
aagcacgcag atcagcgcac attaccgctg gtcagc                             1476
```

<210> SEQ ID NO 5
<211> LENGTH: 789
<212> TYPE: DNA
<213> ORGANISM: Mycobacterium intracellulare

<400> SEQUENCE: 5

```
atgccgccgg ccgcgttcgc ggtgggtgtg atccctggtg gcccgcagac attcgcgctc      60
aagacggtgc tggactgctt gatggcgttc gcggcgatgg tcgtctacac cgcggctttc     120
ggggcctaca acgtcgtgct ggaccgcgtc tatgcggact ccggcggcaa cgtcatcaag     180
gcgatgttcc tgaccgccct ggtgctggcg ttcgggttcg cgttcttcgg gccgctgcgg     240
cggatgttcg atcggcagcg cgacacgatg gccgccaagc tgtctggcgg cggtggcgcg     300
gcgtctggcg gcgggcgtgg tctgttgcag cgggccgcgg acgtgtcgag ctgcgaaat      360
gacttacggc gcaagccgaa acccgacgac gatgacggcg acaatccacg aaacccgccg     420
ccgcgcattg acagtgaatc agattcagcg agcgcgagcg gtggcggtgg tccgtccggt     480
ggcggtccgt caggcggtgg tggaggtgga ccgtctggcg gtggcggcgc tggtgcgtcg     540
tcgggtggcc cgtctggtgg tggcggcggt gagccagatt caggcgcgac ctaccttgac     600
```

```
ggcgacccgg caccggtcag cggtggccgg cgcagcagtg ccccggccgg agaaccggcc    660
tacgccgaca atgggagccg aggcggggac cgactggccg cggcgatgcg gctctaccga    720
gccacccgcg gcgacgcctc accgccggca gggccggact cgtcccggca cgcgctgtca    780
gaggccgca                                                            789

<210> SEQ ID NO 6
<211> LENGTH: 597
<212> TYPE: DNA
<213> ORGANISM: Mycobacterium intracellulare

<400> SEQUENCE: 6
atgcgcccgt atcagcgcga gttgatgggg ccgcggacac acgagcagtg gcgccggttc     60
ttcgcgcata ccccgcaggc cgcgccgatg ccggccggga tcgagttggc caatgcgctg    120
taccggctgg gatggcggta tgcgatctcc acgacccgac cgccgtggaa tggcggcatg    180
gtgagccggt gggtgcgcca gtacctaccg ggccgcgccg aatggatcta cgtcagcggc    240
ggtgaaggcc gtcgccccgc cgaacacaag cgcgaccact acatcgaggc gatggtgtcc    300
cgcggcccgg tgtgcgggct gttcgttgac gacgaaaccg cggtggtcga tcagctcatc    360
gagttcgacc taccagccat gcacattgac gaactggcgg gctgtccga  cgccgccctg    420 accgagctgc tggcctacag cgtgaagaac gccgacgcgc cgccgcggaa actgcgcgcc    480
gaggcccgcg ccgagggcac cagcaccaac cgcgacgagc tgctaaggga gcactaccag    540
cgcgtcaaac agacagccga daccgacgat gcacagggag ccgatcaggt gccggaa       597

<210> SEQ ID NO 7
<211> LENGTH: 2415
<212> TYPE: DNA
<213> ORGANISM: Mycobacterium intracellulare

<400> SEQUENCE: 7
atgagcgcta tcgagtaccc gccgtcgaaa tacgctgacc tgattttggt cagtgaaaag     60
ggcatgcact ggccggagca atcggagtac gtgtggcgga cgtactccga gcaattgaag    120
gccgaatggg gtcgattgat agatcaagag ttcgcccagc agagcatcaa acagaacctc    180
gatgggcaga cgtccgtggg catgattccg gccattaatc agatggtcgc aaagcgcgat    240
gggacgctcg ctgatcgcat cgccgcgctg ccgtcgcga gccctgccgg cgactcgatt     300
cgggcgtcaa tagtggacct caaatccgat ctgtactggg tggtgatgag cgcggatcag    360
aggatcaaag acctcgaaag caaggcgggt attgggctg cggcgaccct gccagcgcag     420
atagcggcga tcatagaagc tgcccaagcc gaggcactcg ccagggacac agcccgcgcc    480
gccgaggtga ccgccaagac caccgaactg ctgtcgtggt cgccgccgtc tggcagcgcc    540
aaacaaagtg gcgggccggg cgcggctaca ccgctctcta cagggatagg cggtgagggg    600
gcctattcgc cgcctctttc accgccaat  ggcagtggag tgcaggccgt cgactacaac    660
acgatgaaac agggttcgcc cgccgacgcc gctcatgggg acgcgaaaca ggccgagaaa    720
ccgtcgctat ctaacgaggc ccgtaaagct gcgtggaagc cgaatgcgct ggacccgaaa    780
gacgctgcgg cggctaaccc ggatcggccg ttgccgtcgc cggcgcattc gtcgccgccg    840
atgtcgtctc cgtcgtcggg gggttcgtcg gcatcgtcgg gcggtgggtc gtcgatgatc    900 ggcagatga tgccacggtc gatgtcgccg tccccggcgt cctcgtcgtc gcccgcctcg    960
tcgggtagcg ggctgtcgtc aggtggtggc ccagcgtcag cgtccccggc cgctgggcac   1020
gcgggcgggc cgggttcccc ggccggtgcg ggtgcgcctg gtgccgcgca aggcggcgcg   1080
```

```
tcggggttgc gtggtgcggg cttggccagt gccgggtctg gtatcgctga gtcgtcggcg      1140
cggctggcgt cgggcgcggt caacgcgacc gcgaacaccc ttggtgcggc gggcaatatc      1200
gggtctcagg tggcccaggg cgcggcgtcg gccgcgtcgg ctgccgcgcc agcggccccg      1260
gctgctgcgc cgccagcggc ggcatcagcc ccggtttctg cgcgcaccggt cggcggtgcg     1320 ccaatcggga tgatgccggc cgctgctgcc ggtggacctg cggtggtcag tccggtcggc      1380
ggtccggtgg ttggtggtgg gccggctgcg acgccggccg cggctgcgac accggtatcg     1440
agtgtgggcg gtgcgacccc ggccgcggcg ggttcgtctc tggccccggt cccgttgcac      1500
acgacgccgg gtgtgcgtgg tgtcggcgcg gacggcgcaa ccggcgatgt gctgttcggg      1560
caggcgatgg atgtgggccg cgacgtggtg tcggcgatgg tggcccagac cgtgtgggcc      1620
ggccatatca cgattcatta cgcggtggcg ctggtgtacg agcggggcgg cacggtggcg      1680
gcgtggatgg ccaccagtga gggagcgtcc tatatcccgc tgggtgtgcg gattccgccg      1740
gatgtgcggc tgtcggtcac cgaccctgtg atcggccgcg agctgtggga gtcgtccgcg      1800
agtgccggcg gggcgaaccc ccttgccacc gtggtgcgtc aggcacagga gcgcgagatg      1860
gccgcacccg gtagccgggt gctggcggta gcgtcgtcac tgcccatgga tcaggtgact      1920
gactacgccc ccgaggtgtc ggcgcggcg gtgcacgtgg acccgaaatc catcaccaaa      1980
ccggccgggg tggatatggc gatggcgcat cggtgcgcgg tcgcgatgcc gtgggaatgg     2040
cagcaagcca acaggtttga cgaacaggag cggtaccgca tcgcctcccg gcacatgtac      2100
atggcgatga gtaccggacg actcagcagc ggtgcatgcg aggaagtcat ggacctgtac      2160
gagctgggga agccggtccc ggaagcgctg tggcgcgagg tcaacaacgc gaggctcaag      2220
ccgctgaccg agtacatgct ggcgatgcag tcagccgggc agggtggggc tgtaccagtg      2280
cgagcgctgg cggcggcgcg ggccgccgag gtgatcctgt gcctgcgcca cagcacgacc      2340
gccgaggggt gcgcggattt gctttatgcc tcccggttgg cgggtgctcc gctagaaccg      2400
aacgcggccg tggca                                                       2415

<210> SEQ ID NO 8
<211> LENGTH: 360
<212> TYPE: DNA
<213> ORGANISM: Mycobacterium intracellulare

<400> SEQUENCE: 8
atgagcagca ctgacaacac tctgaacgtg tcaccggaga ggctggccgc gggcgcggcg       60
acggccggtg ctacggaaac cgccagcgtg ccagcccctt tggtcccgcc gccacccggc      120
gggacatcac tgctggacat cgccgcaggc gcggcggcta acgccatcgt ggcgatgatc      180
gccaaggccg acgccgccga cgccgccgca gcgggcacac agacggcctc actcaccgag      240
tccccgccga ccgtggtgca gcaagaccaa caagcagccg gcgactacca gcgatccgta      300
accttcccaa taccggcggt gacgccgcta gcaccgggaa ccggccaggt gttcacggtc      360

<210> SEQ ID NO 9
<211> LENGTH: 1245
<212> TYPE: DNA
<213> ORGANISM: Mycobacterium intracellulare

<400> SEQUENCE: 9
atgtggtcgt cgcgggagtt gtggactgcc gatctgcggg tgcttttgtc gggtccggag       60
ttcagcacgc gccgggtgat ttcggcgcg acgtgctcg ctgtcgcggt ggcgatggcc        120
gagttcgccg accatgccac gggccgcaat gtggcggtga caaacgaggt tctggccgag     180
```

```
cgcgcgaggt gttctaagcg ttcggtgacc cgggcgcgcg gggtgttgaa agcgttgggt    240
gtcgcggtgg aagcggtacg tgggcatggc tctgcgacca cacacacggt cggtaatcga    300
ccgagcattt ggcacctggt aagccgacgc cagcccacca tcgacaaccc gcccacggcc    360
ccgcagaacg gccgcggcga gcctgccgat acggtgcccg atcgcggcca gagcgcgccc    420
gtggctgtgg agacttgcga cctaccacca tcccgtaggg ataggtgggt aactcctgtt    480
gagaattact caccaagcac gcgcgagcgc gcgagcgcgg aaaattcttc cccaaaacaa    540
acacaaccgg cgcggtcgcg gcggcgctac cgcgccacgc cgcgccccct ggacgttcag    600
cgactcgccg ccggcctggt cacgccggca gtcggcacg gcccagacaa cgacgggcgg     660
cgaaccgcgc tgatcgccgg cctggagcag ggccatatcg gggccatctg cgacgcgatc    720
acgacggccg gcatcgacgc gaccgcctgg actccgaaga cgctcacggc ggcactgaac    780
gccgacgcgc gggtgaccgg ctggtcgtgg ccggatcgca tcgaacgtcc tggcgcgttc    840
ctggcgtcgc ggctgcgccg cctgcccgca cggcccgaca ccagtggccc ggttgacaac    900
ggcctggatc aggcccgtag acacccgtt gagccgtcag cggcccgtgt agcgccggta     960
cagacggccg ctggccgcgc gtacgcccgt gcgttgttcg ccgagcagcg acggcaccgg   1020
gtgaccgccg ccaatgccca gtcagccgcg gtgccggtgc gccaaagtgc gccagaaacc   1080
gcggtgtgcg caacgtgcgg atgctcggac gcaccacggc ggcggttcct gccaacgcgg   1140
cgggctcaca tttgcgatgc ctgtttccaa ggatgtggtg gtgggcaggc gcgtactggt   1200
cgcgtcggaa cggtcggcag cagttccgcg gtgccacagt gccag                   1245

<210> SEQ ID NO 10
<211> LENGTH: 1089
<212> TYPE: DNA
<213> ORGANISM: Mycobacterium intracellulare

<400> SEQUENCE: 10
atgggtgagc cacagccgcg ctggccgcac acgggcgcgt tccccgagtg gacctggcaa     60
gtgtcggaca acctgcgcca gaccaccacc gatggcttgc gccgggcaca ggacggcaag    120
cggttggccg atctgaacgg caacgccgag gcatctagga attacgggtt tcagatcgaa    180
atctacgaac agtacgccgc tgagctggac cagcgcgacg ccgaggcccg cgaccagtac    240
gcacgtgagc acagcgaatg gcgagaccgc aattcgtata tcggttcgcg taacgggttg    300
tgggccgatg tgctgcggtg ggcgcgcagc ggcgaactgc ccgccgactg gcgtagccat    360
ctgcccggct actgcgcccg catcgccgcc atcgccggtg aagaactgcg cgacgacatc    420 gacgcctgg tcctgcacga gttcaccacc ctgccaccgc aaccgtggga gccctacgcc    480
actggcgggg actggcgcac cgcgctcgac gcctggtacc gcgacagcct tgccctgcac    540
gaccgcaccc accagcagga cgaggaactg aacgcaagca aaccgcaaca gttccgactg    600
cctccgccca tgccaggccc ctacgacgcc ccgtcgccag ccatcatcga catgacccgg    660
cgcgggttca tggacgaagc cgacagagcc ctccgtgacg cggactgggc tgcggcccag    720
accatcaacc acgcacgggg ccgtgatcgc ctcgaagcgt ggtaccgggc cgggctcacc    780
gccggcggca ccggcgaaga ctggacaggc tggtaccgcg accgcatcac caacacgtgg    840
gaccgccgcc acgacgacat ctacggtgcc aagctgatcg catccgaccg cgagctggcg    900
cggctggacg acgccctaa cgcgacactg gacccatcgc cggccgcggc cggcggatgg    960
gtccgcatcc ccgtgcaagc cctgcccgac tactggcact gtggcaccgc ggaactgctg   1020
```

```
ccgaccgttc cgacgcgacc agtacgcgcc tgcccaccac cacatccttg gaaacaggca    1080
tcgcaaatg                                                            1089

<210> SEQ ID NO 11
<211> LENGTH: 648
<212> TYPE: DNA
<213> ORGANISM: Mycobacterium intracellulare

<400> SEQUENCE: 11
atgacacctc cacgtgtgac cagctttgtg aaccaaaaag gcggggtcgg caaaagcacg      60
ctggccgtca acgtcgccgc cgagaaagcc cgccgcggcc ggcgcgtact gctgctcgac    120
gccgaccagc aaggtacggc gctggactgg caggcccaac gcggccggct ggaacacccg    180
ccgctgatgt cggtggtcgg gttcccgcga gacaccatcc accgagaaat cggccaactc    240
ggggagggct acgacgacat catcatcgac gcacccggcc gcgtcgaagc cgtcgcccgc    300
gccgtgatca tggcctccga tgtcgtggtc atccccgtac agcccagcgc gtacgacata    360
tgggccagcg ccgacgtgct caccctgctc gagcaatccc agatctataa gcccgtgatc    420
gccgtgtggg tgatcaaccg gcgcatcgtt aacaccaaga tcgcccgtga cgtgaaacag    480
cagctcagtg aatatgggcc acgcctgctg gaggctaacg tcgccaaccg ggtcatctac    540
tccgaagcca acggtctcgg gctggccgtg tacgaatccg accccggcgg ggtcgctgac    600
gacgaaatcc gcgcagtcac caccgaattg gaggcaatca accatggc                 648

<210> SEQ ID NO 12
<211> LENGTH: 1884
<212> TYPE: DNA
<213> ORGANISM: Mycobacterium intracellulare

<400> SEQUENCE: 12
atggatgagc acctgatcat caccggcggg cggacgtacc ggatacctgc cggcgacaac      60
gaggacatgg acgcgcttct ggcgtggtgg gtggagtcgc ggggcgaacc ggcgtcggtg    120
gcagcgttgt cgcgtcagca ggtgttcgcc cggattcgcc gggcggcgat cccggccggg    180
ttcccggagc ccgatgtggt gatcggtgac accgaccgcg acagcggcgg gtttgtccgc    240
ggctggctgc cggcgacggt gcaggcatgg caagacgaac aagacaagcc ggccgcttcc    300
ggcgcgccca ccgagccggc cgcggccggt gagccggtcg gccaggacga accgcgccg     360 gctgatcccg gcccggccgc tggtgacgat gaggacgtgt ggcggatggg tgcacgccgg    420
tggaccggtg tgggcgatcg ggccgacaag ttcgtgcgca tcctgacgag ccgcggcgcg    480 ctcacccgt ccggggtggt gtcggcgcgg gtaccgctgg atgccgcatt gctgggccag    540
tacgtgtgga agcactggcc gcagaaaccg gcgcagacac cacagctgtg ggtgacagcg    600
ccggcgttgg cggcggcggg gatgagcccg ccgaagcggc ccccgacgac ctcggaggac    660
ttgtccgacg cggtggccaa ggcgttcggt tgtgaagtca ccgcggcgac ggccggatgg    720
ttcaccgcgc agttccgcga tcccgcgggt ggcgtggagg cgcgccgggt acatctggtg    780
ctgctgccgt tccgctggtt ggacccggcg tcgcagcggc ccaacgatga gggcatggcc    840
ggcactcgcg gcgctgcgtc cgagctgccc gacgacgagg acaacgagga cgccgcggtg    900
gcggtgctgg gtgagcgcat cgcgtggctg gcggcgctgg ccgacaagac cgacagccac    960
cgccgggagc tgccggtggt gccgcggcg cggccggcaa cggtcgggc ggcgctgctg     1020 gacgtggtac gcaaacgtga acgcaaaccg caccggttgg aggcgttccc ggtgcccgac    1080
accgtggccg ctgaaacacc acgcctggac cccgattggg agaactggaa gaacatgccg    1140
```

```
cacaccgcca aaggtgatgc ggtcgatgtc gaggttgatc agcgggcagc gtttttggcc   1200
agcacagggc aggtggaatt gggatatggc cggccggtgg agatgcccaa ggtggacgcc   1260
gcggtgttcg ccgacaaacc gccgttcggg ctgtggcggg tgaccacgcc gccagcggca   1320
tcgttggacg gcctgagccg ccgcctgccg ctgccgcacg aatacatggc atgggaggcc   1380
ccggcgacgt tttgggcgac gacacgggcc gttcagcact tgctggcgcc ggtggacgac   1440
ggcggcgcgg gggtgtcgat cggtgagttg gcgatcgacg gggcatgggt gtggccgggg   1500
catgcccggc tgctgcgcaa ctgggcggac ctgctgcggg atcggctggc cgcggcgctg   1560
gcggatggcg accagttcca gacggacatg ctcaaaaaca tctacaaggc gtttctgggg   1620
cggatggctg gtagccagca cccaccgggg cagcggcact accagcaacc ggtgtgggtg   1680
gccacaatcc acgcggacac ccgctggcgg gccatgcgct acgccaccgc caccgcggcc   1740
acgcacggtc tgtatccgat cgcggcccgc gacatcgaca cgttcgtcta ccggattccg   1800
gcggacatgg accccgcggt gctgagtgaa gaatcgaccg ccaacggtaa gtaccgggtc   1860
aaaaaggtca ggaccggtga ccac                                         1884

<210> SEQ ID NO 13
<211> LENGTH: 321
<212> TYPE: DNA
<213> ORGANISM: Mycobacterium intracellulare

<400> SEQUENCE: 13
atgcgcggag aactttggac ggcctccggc cgcgactacg ccggcaaacc acggccggtg   60
ctcgtcgtcc aggacgaccg tttcgacgcc acagattccg tcacaatctg cccctcaca    120 accaacacca cgggtgcacc cctgctgcga ataccgtgc agcccaacgc ctccaacgga   180
ctcacaacac cgagccacat catgatcgac aaaatcacca cggttcccag gtccaagatc   240
ggccagcgca tcggcaaggt atcgaccacc gaaatgctcc agctcgaacg cggcctactc   300
gtcttcctcg gaatgaccgg a                                            321

<210> SEQ ID NO 14
<211> LENGTH: 525
<212> TYPE: DNA
<213> ORGANISM: Mycobacterium intracellulare

<400> SEQUENCE: 14
atgaaaccgc aactccaagt cgggcactgg tatctcgtgc acgtagaagg aaaacacacc   60
tctgtcaggg cctacatgga aggcggctgg taccgcgcg acccgtggcc caccaaagca   120
ctctgcgaaa tgagccgcgt cggcaacccg taccacccccg acgacatcga gctacccgac   180
aaacccgatg tcaccgaaat cgaccgcgcc ctgatcgagc agcactaccc gccgccaag    240 actcaccgcgc tgatcgccgg cgcgatctac aacatggcca tgggcctgtg cctggccaac   300
ggcaaagagt ggaactggga actgcccgac gccgatccgc aaccccatat cgactccctg   360
gtcctcgcgt gctcggtgct caccgacatg gtcggcccga acgcgtcgt ccgggacatc   420 accgacatgg aagccaccag cggccccgcca atgggctggt tccggccccg caagtggccc   480
agcgagatca tccccggagc cgtgcctctc ggcgaaatcg ccgcg                   525

<210> SEQ ID NO 15
<211> LENGTH: 177
<212> TYPE: DNA
<213> ORGANISM: Mycobacterium intracellulare
```

<400> SEQUENCE: 15

```
atgacctctg gcgatcgtga agacgagcac cgccgcggca tcacgctggc tcagatcaaa      60
cgggctggcc tctacaccag gccaacgtcg ccgggctacc ggcaagccat gctggacatg     120
gttgagcgtg ccgcgacga cgccggccgc ataggcgaca cagaacgacc ccagcgg         177
```

<210> SEQ ID NO 16
<211> LENGTH: 133
<212> TYPE: PRT
<213> ORGANISM: Mycobacterium intracellulare

<400> SEQUENCE: 16

```
Met Val Ser Gly Ser Glu Cys Arg Val Lys Ser Val Phe Asp Glu Leu
1               5                   10                  15

Thr Ser Asp Glu Leu Ala Ala Thr Ala Asp Ala Ala Ala Gly
            20                  25                  30

Leu Glu Ala Ala Arg Leu Thr Ala Ala Arg Leu Ala Lys Gly Pro
        35                  40                  45

Ala Val Gly Val Gly Arg Pro Ala Ala Leu Val Lys Leu Leu Met Gly
    50                  55                  60

Arg Asn Glu Ala Asp Pro Thr Trp Glu Arg Leu Ala Pro Phe Glu Gln
65                  70                  75                  80

Arg Trp Ala Leu Leu Val Val Arg Ile Val Gly Ala Val Met Asp Pro
                85                  90                  95

Val Ser Ala Val Ala Asp Ala Arg Arg Arg Gly Ala Ser Trp Ala Ala
            100                 105                 110

Val Gly Ala Val Leu Gly Val Ser Ala Gln Ala Ala His Gly Arg Phe
        115                 120                 125

Ala Ser Arg Met Gly
    130
```

<210> SEQ ID NO 17
<211> LENGTH: 492
<212> TYPE: PRT
<213> ORGANISM: Mycobacterium intracellulare

<400> SEQUENCE: 17

```
Met Thr Asp Val Glu Leu Ser Ala Tyr Arg Phe Ala Leu Asp Thr Thr
1               5                   10                  15

Pro Ala Gln Leu Thr Met Leu Arg Gln His Ala Gly Ala Ala Arg Trp
            20                  25                  30

Ala Tyr Asn His Ala Leu Gly Val Lys Phe Ala Ala Leu Asp Glu Arg
        35                  40                  45

Lys Thr Val Ile Ala Gly Leu Val Glu Gln Gly Leu Asp Pro Lys Thr
    50                  55                  60

Ser Ala Ala Gln Ala Pro Lys Ile Pro Thr Lys Pro Ala Ile Gln Lys
65                  70                  75                  80

Ala Leu Asn Thr Thr Lys Gly Asp Asp Arg Ile Ser Ala Ala Gly Asp
                85                  90                  95

Cys Pro Trp Trp His Thr Val Ser Thr Tyr Ala Phe Gln Ser Ala Phe
            100                 105                 110

Ala Asp Ala Asp Thr Ala Trp Lys Asn Trp Leu Ala Ser Leu Thr Gly
        115                 120                 125

Lys Arg Ser Gly Pro Ile Gly Ala Pro Arg Phe Lys Ser Lys His Arg
    130                 135                 140
```

```
Ser Arg Asp Ser Phe Arg Ile His His Asp Val Asn Asn Pro Thr Ile
145                 150                 155                 160

Arg Pro Asp Asp Gly Tyr Arg Arg Ile Ile Val Pro Arg Leu Gly Ser
                165                 170                 175

Leu Arg Val His Asp Ser Thr Lys Arg Leu Lys Arg Ala Ile Asp Arg
            180                 185                 190

Gly Ala Val Ile Gln Ser Val Thr Ile Ser Arg Gly Gly His Arg Trp
        195                 200                 205

Tyr Ala Ser Ile Leu Val Lys Ala Pro Ala Ala His Ala Ala Pro Thr
    210                 215                 220

Arg Arg Gln Arg Gln Ala Gly Thr Val Gly Val Asp Leu Gly Val His
225                 230                 235                 240

His Leu Ala Ala Leu Ser Thr Gly Asp Ile Ile Asp Asn Pro Arg His
                245                 250                 255

Leu Ala Ala Gly Gln Lys Arg Leu Thr Lys Ala Gln Arg Ala Leu Ser
            260                 265                 270

Arg Thr Glu Lys Gly Ser Asn Arg Arg Arg Arg Ala Ala Ala Arg Val
        275                 280                 285

Gly Arg Arg His His Glu Ile Thr Glu Arg Arg Ala Thr Thr Leu His
    290                 295                 300

Thr Leu Thr Lys His Leu Ala Thr Asn Trp Ala Thr Val Ala Ile Glu
305                 310                 315                 320

Asp Leu Asn Val Ala Gly Met Thr Arg Ser Ala Arg Gly Thr Ile Asp
                325                 330                 335

Asn Pro Gly Thr Asn Val Arg Ala Lys Ala Gly Leu Ser Arg Ala Ile
            340                 345                 350

Leu Asp Thr Ser Pro Gly Glu Leu Arg Arg Gln Leu Thr Tyr Lys Thr
        355                 360                 365

Gly Trp Tyr Gly Ser Thr Leu Ala Ile Cys Asp Arg Trp Phe Pro Ser
    370                 375                 380

Ser Gln Gln Cys Cys Glu Cys Lys Val Arg Thr Lys Leu Arg Leu Ser
385                 390                 395                 400

Gln Arg Val Phe Thr Cys Pro Ala Cys Gly Tyr Gly Pro Ile Asp Arg
                405                 410                 415

Asp Val His Ala Ala Arg Asn Ile Ala Ala Tyr Ala Ala Val Ala Ser
            420                 425                 430

Asp Thr Gly Glu Thr Leu Thr Ala Arg Arg Asp Thr Ala Glu Ala Pro
        435                 440                 445

Thr Arg Val Gly Arg Arg Arg Gly Ala Val Asp Ala Gly Arg Pro His
    450                 455                 460

Arg Glu Thr Gly Ala Ala Thr Pro Ala Glu Gln Pro Ala Gly His Pro
465                 470                 475                 480

Lys His Ala Asp Gln Arg Thr Leu Pro Leu Val Ser
                485                 490

<210> SEQ ID NO 18
<211> LENGTH: 263
<212> TYPE: PRT
<213> ORGANISM: Mycobacterium intracellulare

<400> SEQUENCE: 18

Met Pro Pro Ala Ala Phe Ala Val Gly Val Ile Pro Gly Gly Pro Gln
1               5                   10                  15

Thr Phe Ala Leu Lys Thr Val Leu Asp Cys Leu Met Ala Phe Ala Ala
            20                  25                  30
```

Met Val Val Tyr Thr Ala Ala Phe Gly Ala Tyr Asn Val Leu Asp
            35                  40                  45

Arg Val Tyr Ala Asp Ser Gly Gly Asn Val Ile Lys Ala Met Phe Leu
 50                  55                  60

Thr Ala Leu Val Leu Ala Phe Gly Phe Ala Phe Phe Gly Pro Leu Arg
 65                  70                  75                  80

Arg Met Phe Asp Arg Gln Arg Asp Thr Met Ala Ala Lys Leu Ser Gly
                 85                  90                  95

Gly Gly Gly Ala Ala Ser Gly Gly Arg Gly Leu Leu Gln Arg Ala
                100                 105                 110

Ala Asp Val Ser Arg Leu Arg Asn Asp Leu Arg Lys Pro Lys Pro
            115                 120                 125

Asp Asp Asp Asp Gly Asp Asn Pro Arg Asn Pro Pro Arg Ile Asp
            130                 135                 140

Ser Glu Ser Asp Ser Ala Ser Ala Ser Gly Gly Gly Pro Ser Gly
145                 150                 155                 160

Gly Gly Pro Ser Gly Gly Gly Gly Pro Ser Gly Gly Gly
                165                 170                 175

Ala Gly Ala Ser Ser Gly Gly Pro Ser Gly Gly Gly Gly Glu Pro
            180                 185                 190

Asp Ser Gly Ala Thr Tyr Leu Asp Gly Asp Pro Ala Pro Val Ser Gly
            195                 200                 205

Gly Arg Arg Ser Ser Ala Pro Ala Gly Glu Pro Ala Tyr Ala Asp Asn
    210                 215                 220

Gly Ser Arg Gly Gly Asp Arg Leu Ala Ala Ala Met Arg Leu Tyr Arg
225                 230                 235                 240

Ala Thr Arg Gly Asp Ala Ser Pro Pro Ala Gly Pro Asp Ser Ser Arg
                245                 250                 255

His Ala Leu Ser Glu Ala Ala
                260

<210> SEQ ID NO 19
<211> LENGTH: 199
<212> TYPE: PRT
<213> ORGANISM: Mycobacterium intracellulare

<400> SEQUENCE: 19

Met Arg Pro Tyr Gln Arg Glu Leu Met Gly Pro Arg Thr His Glu Gln
 1               5                  10                  15

Trp Arg Arg Phe Phe Ala His Thr Pro Gln Ala Ala Pro Met Pro Ala
                20                  25                  30

Gly Ile Glu Leu Ala Asn Ala Leu Tyr Arg Leu Gly Trp Arg Tyr Ala
            35                  40                  45

Ile Ser Thr Thr Arg Pro Pro Trp Asn Gly Gly Met Val Ser Arg Trp
 50                  55                  60

Val Arg Gln Tyr Leu Pro Gly Arg Ala Glu Trp Ile Tyr Val Ser Gly
 65                  70                  75                  80

Gly Glu Gly Arg Arg Pro Ala Glu His Lys Arg Asp His Tyr Ile Glu
                 85                  90                  95

Ala Met Val Ser Arg Gly Pro Val Cys Gly Leu Phe Val Asp Asp Glu
                100                 105                 110

Thr Ala Val Val Asp Gln Leu Ile Glu Phe Asp Leu Pro Ala Met His
            115                 120                 125

Ile Asp Glu Leu Ala Gly Leu Ser Asp Ala Ala Leu Thr Glu Leu Leu
            130                 135                 140

```
Ala Tyr Ser Val Lys Asn Ala Asp Ala Arg Arg Lys Leu Arg Ala
145                 150                 155                 160

Glu Ala Arg Ala Glu Gly Thr Ser Thr Asn Arg Asp Glu Leu Leu Arg
                165                 170                 175

Glu His Tyr Gln Arg Val Lys Gln Thr Ala Glu Thr Asp Asp Ala Gln
            180                 185                 190

Gly Ala Asp Gln Val Pro Glu
        195

<210> SEQ ID NO 20
<211> LENGTH: 805
<212> TYPE: PRT
<213> ORGANISM: Mycobacterium intracellulare

<400> SEQUENCE: 20

Met Ser Ala Ile Glu Tyr Pro Pro Ser Lys Tyr Ala Asp Leu Ile Leu
1               5                   10                  15

Val Ser Glu Lys Gly Met His Trp Pro Glu Gln Ser Glu Tyr Val Trp
            20                  25                  30

Arg Thr Tyr Ser Glu Gln Leu Lys Ala Glu Trp Gly Arg Leu Ile Asp
        35                  40                  45

Gln Glu Phe Ala Gln Gln Ser Ile Lys Gln Asn Leu Asp Gly Gln Thr
    50                  55                  60

Ser Val Gly Met Ile Pro Ala Ile Asn Gln Met Val Ala Lys Arg Asp
65                  70                  75                  80

Gly Thr Leu Ala Asp Arg Ile Ala Ala Leu Ala Val Ala Ser Pro Ala
                85                  90                  95

Ala Asp Ser Ile Arg Ala Ser Ile Val Asp Leu Lys Ser Asp Leu Tyr
            100                 105                 110

Trp Val Val Met Ser Ala Asp Gln Arg Ile Lys Asp Leu Glu Ser Lys
        115                 120                 125

Ala Gly Ile Gly Ala Ala Ala Thr Leu Pro Ala Gln Ile Ala Ala Ile
    130                 135                 140

Ile Glu Ala Ala Gln Ala Glu Ala Leu Ala Arg Asp Thr Ala Arg Ala
145                 150                 155                 160

Ala Glu Val Thr Ala Lys Thr Thr Glu Leu Leu Ser Trp Ser Pro Pro
                165                 170                 175

Ser Gly Ser Ala Lys Gln Ser Gly Gly Pro Gly Ala Ala Thr Pro Leu
            180                 185                 190

Ser Thr Gly Ile Gly Gly Glu Gly Ala Tyr Ser Pro Pro Leu Ser Pro
        195                 200                 205

Ala Asn Gly Ser Gly Val Gln Ala Val Asp Tyr Asn Thr Met Lys Gln
    210                 215                 220

Gly Ser Pro Ala Asp Ala Ala His Gly Asp Ala Lys Gln Ala Glu Lys
225                 230                 235                 240

Pro Ser Leu Ser Asn Glu Ala Arg Lys Ala Ala Trp Lys Pro Asn Ala
                245                 250                 255

Leu Asp Pro Lys Asp Ala Ala Ala Asn Pro Asp Arg Pro Leu Pro
            260                 265                 270

Ser Pro Ala His Ser Ser Pro Met Ser Ser Pro Ser Gly Gly
        275                 280                 285

Ser Ser Ala Ser Ser Gly Gly Gly Ser Ser Met Ile Gly Gln Met Met
    290                 295                 300

Pro Arg Ser Met Ser Pro Ser Pro Ala Ser Ser Ser Ser Pro Ala Ser
305                 310                 315                 320
```

```
Ser Gly Ser Gly Leu Ser Ser Gly Gly Pro Ala Ser Ala Ser Pro
            325                 330                 335

Ala Ala Gly His Ala Gly Gly Pro Gly Ser Pro Ala Gly Ala Gly Ala
            340                 345                 350

Pro Gly Ala Ala Gln Gly Gly Ala Ser Gly Leu Arg Gly Ala Gly Leu
            355                 360                 365

Ala Ser Ala Gly Ser Gly Ile Ala Glu Ser Ser Ala Arg Leu Ala Ser
            370                 375                 380

Gly Ala Val Asn Ala Thr Ala Asn Thr Leu Gly Ala Ala Gly Asn Ile
385                 390                 395                 400

Gly Ser Gln Val Ala Gln Gly Ala Ala Ser Ala Ala Ser Ala Ala Ala
            405                 410                 415

Pro Ala Ala Pro Ala Ala Ala Pro Pro Ala Ala Ala Ser Ala Pro Val
            420                 425                 430

Ser Gly Ala Pro Val Gly Gly Ala Pro Ile Gly Met Met Pro Ala Ala
            435                 440                 445

Ala Ala Gly Gly Pro Ala Val Val Ser Pro Val Gly Gly Pro Val Val
            450                 455                 460

Gly Gly Gly Pro Ala Ala Thr Pro Ala Ala Ala Thr Pro Val Ser
465                 470                 475                 480

Ser Val Gly Gly Ala Thr Pro Ala Ala Ala Gly Ser Ser Leu Ala Pro
            485                 490                 495

Val Pro Leu His Thr Thr Pro Gly Val Arg Gly Val Gly Ala Asp Gly
            500                 505                 510

Ala Thr Gly Asp Val Leu Phe Gly Gln Ala Met Asp Val Gly Arg Asp
            515                 520                 525

Val Val Ser Ala Met Val Ala Gln Thr Val Trp Ala Gly His Ile Thr
            530                 535                 540

Ile His Tyr Ala Val Ala Leu Val Tyr Glu Arg Gly Gly Thr Val Ala
545                 550                 555                 560

Ala Trp Met Ala Thr Ser Glu Gly Ala Ser Tyr Ile Pro Leu Gly Val
            565                 570                 575

Arg Ile Pro Pro Asp Val Arg Leu Ser Val Thr Asp Pro Val Ile Gly
            580                 585                 590

Arg Glu Leu Trp Glu Ser Ser Ala Ser Ala Gly Gly Ala Asn Pro Leu
            595                 600                 605

Ala Thr Val Val Arg Gln Ala Gln Glu Arg Glu Met Ala Ala Pro Gly
            610                 615                 620

Ser Arg Val Leu Ala Val Ala Ser Ser Leu Pro Met Asp Gln Val Thr
625                 630                 635                 640

Asp Tyr Ala Ala Glu Val Ser Ala Arg Pro Val His Val Asp Pro Lys
            645                 650                 655

Ser Ile Thr Lys Pro Ala Gly Val Asp Met Ala Met Ala His Arg Cys
            660                 665                 670

Ala Val Ala Met Pro Trp Glu Trp Gln Gln Ala Asn Arg Phe Asp Glu
            675                 680                 685

Gln Glu Arg Tyr Arg Ile Ala Ser Arg His Met Tyr Met Ala Met Ser
            690                 695                 700

Thr Gly Arg Leu Ser Ser Gly Ala Cys Glu Glu Val Met Asp Leu Tyr
705                 710                 715                 720

Glu Leu Gly Lys Pro Val Pro Glu Ala Leu Trp Arg Glu Val Asn Asn
            725                 730                 735
```

```
Ala Arg Leu Lys Pro Leu Thr Glu Tyr Met Leu Ala Met Gln Ser Ala
                740                 745                 750

Gly Gln Gly Gly Ala Val Pro Val Arg Ala Leu Ala Ala Ala Arg Ala
            755                 760                 765

Ala Glu Val Ile Leu Cys Leu Arg His Ser Thr Thr Ala Glu Gly Cys
        770                 775                 780

Ala Asp Leu Leu Tyr Ala Ser Arg Leu Ala Gly Ala Pro Leu Glu Pro
785                 790                 795                 800

Asn Ala Ala Val Ala
            805

<210> SEQ ID NO 21
<211> LENGTH: 120
<212> TYPE: PRT
<213> ORGANISM: Mycobacterium intracellulare

<400> SEQUENCE: 21

Met Ser Ser Thr Asp Asn Thr Leu Asn Val Ser Pro Glu Arg Leu Ala
1               5                   10                  15

Ala Gly Ala Ala Thr Ala Gly Ala Thr Glu Thr Ala Ser Val Pro Ala
            20                  25                  30

Pro Leu Val Pro Pro Pro Gly Gly Thr Ser Leu Leu Asp Ile Ala
        35                  40                  45

Ala Gly Ala Ala Ala Asn Ala Ile Val Ala Met Ile Ala Lys Ala Asp
    50                  55                  60

Ala Ala Asp Ala Ala Ala Gly Thr Gln Thr Ala Ser Leu Thr Glu
65                  70                  75                  80

Ser Pro Pro Thr Val Val Gln Gln Asp Gln Gln Ala Ala Gly Asp Tyr
                85                  90                  95

Gln Arg Ser Val Thr Phe Pro Ile Pro Ala Val Thr Pro Leu Ala Pro
            100                 105                 110

Gly Thr Gly Gln Val Phe Thr Val
        115                 120

<210> SEQ ID NO 22
<211> LENGTH: 415
<212> TYPE: PRT
<213> ORGANISM: Mycobacterium intracellulare

<400> SEQUENCE: 22

Met Trp Ser Ser Arg Glu Leu Trp Thr Ala Asp Leu Arg Val Leu Leu
1               5                   10                  15

Ser Gly Pro Glu Phe Ser Thr Arg Arg Val Ile Ser Ala Ala Thr Val
            20                  25                  30

Leu Ala Val Ala Val Ala Met Ala Glu Phe Ala Asp His Ala Thr Gly
        35                  40                  45

Arg Asn Val Ala Val Thr Asn Glu Val Leu Ala Glu Arg Ala Arg Cys
    50                  55                  60

Ser Lys Arg Ser Val Thr Ala Ala Arg Gly Val Leu Lys Ala Leu Gly
65                  70                  75                  80

Val Ala Val Glu Ala Val Arg Gly His Gly Ser Ala Thr Thr His Thr
                85                  90                  95

Val Gly Asn Arg Pro Ser Ile Trp His Leu Val Ser Arg Arg Gln Pro
            100                 105                 110

Thr Ile Asp Asn Pro Pro Thr Ala Pro Gln Asn Gly Arg Gly Glu Pro
        115                 120                 125
```

-continued

```
Ala Asp Thr Val Pro Asp Arg Gly Gln Ser Ala Pro Val Ala Val Glu
    130                 135                 140

Thr Cys Asp Leu Pro Pro Ser Arg Arg Asp Arg Trp Val Thr Pro Val
145                 150                 155                 160

Glu Asn Tyr Ser Pro Ser Thr Arg Glu Arg Ala Ser Ala Glu Asn Ser
                165                 170                 175

Ser Pro Lys Gln Thr Gln Pro Ala Arg Ser Arg Arg Arg Tyr Arg Ala
            180                 185                 190

Thr Pro Arg Pro Leu Asp Val Gln Arg Leu Ala Ala Gly Leu Val Thr
        195                 200                 205

Pro Ala Val Gly His Gly Pro Asp Asn Asp Gly Arg Arg Thr Ala Leu
    210                 215                 220

Ile Ala Gly Leu Glu Gln Gly His Ile Gly Ala Ile Cys Asp Ala Ile
225                 230                 235                 240

Thr Thr Ala Gly Ile Asp Ala Thr Ala Trp Thr Pro Lys Thr Leu Thr
                245                 250                 255

Ala Ala Leu Asn Ala Asp Ala Arg Val Thr Gly Trp Ser Trp Pro Asp
            260                 265                 270

Arg Ile Glu Arg Pro Gly Ala Phe Leu Ala Ser Arg Leu Arg Arg Leu
        275                 280                 285

Pro Ala Arg Pro Asp Thr Ser Gly Pro Val Asp Asn Gly Leu Asp Gln
    290                 295                 300

Ala Arg Arg Thr Pro Val Glu Pro Ser Ala Ala Arg Val Ala Pro Val
305                 310                 315                 320

Gln Thr Ala Ala Gly Arg Ala Tyr Ala Arg Ala Leu Phe Ala Glu Gln
                325                 330                 335

Arg Arg His Arg Val Thr Ala Ala Asn Ala Gln Ser Ala Ala Val Pro
            340                 345                 350

Val Arg Gln Ser Ala Pro Glu Thr Ala Val Cys Ala Thr Cys Gly Cys
        355                 360                 365

Ser Asp Ala Pro Arg Arg Arg Phe Leu Pro Thr Arg Arg Ala His Ile
    370                 375                 380

Cys Asp Ala Cys Phe Gln Gly Cys Gly Gly Gly Gln Ala Arg Thr Gly
385                 390                 395                 400

Arg Val Gly Thr Val Gly Ser Ser Ser Ala Val Pro Gln Cys Gln
                405                 410                 415

<210> SEQ ID NO 23
<211> LENGTH: 363
<212> TYPE: PRT
<213> ORGANISM: Mycobacterium intracellulare

<400> SEQUENCE: 23

Met Gly Glu Pro Gln Pro Arg Trp Pro His Thr Gly Ala Phe Pro Glu
1               5                   10                  15

Trp Thr Trp Gln Val Ser Asp Asn Leu Arg Gln Thr Thr Thr Asp Gly
            20                  25                  30

Leu Arg Arg Ala Gln Asp Gly Lys Arg Leu Ala Asp Leu Asn Gly Asn
        35                  40                  45

Ala Glu Ala Ser Arg Asn Tyr Gly Phe Gln Ile Glu Ile Tyr Glu Gln
    50                  55                  60

Tyr Ala Ala Glu Leu Asp Gln Arg Asp Ala Glu Ala Arg Asp Gln Tyr
65                  70                  75                  80

Ala Arg Glu His Ser Glu Trp Arg Asp Arg Asn Ser Tyr Ile Gly Ser
                85                  90                  95
```

-continued

```
Arg Asn Gly Leu Trp Ala Asp Val Leu Arg Trp Ala Arg Ser Gly Glu
            100                 105                 110

Leu Pro Ala Asp Trp Arg Ser His Leu Pro Gly Tyr Cys Ala Arg Ile
        115                 120                 125

Ala Ala Ile Ala Gly Glu Glu Leu Arg Asp Asp Ile Asp Gly Leu Val
    130                 135                 140

Leu His Glu Phe Thr Thr Leu Pro Pro Gln Pro Trp Glu Pro Tyr Ala
145                 150                 155                 160

Thr Gly Gly Asp Trp Arg Thr Ala Leu Asp Ala Trp Tyr Arg Asp Ser
                165                 170                 175

Leu Ala Leu His Asp Arg Thr His Gln Gln Asp Glu Glu Leu Asn Ala
            180                 185                 190

Ser Lys Pro Gln Gln Phe Arg Leu Pro Pro Pro Met Pro Gly Pro Tyr
        195                 200                 205

Asp Ala Pro Ser Pro Ala Ile Ile Asp Met Thr Arg Arg Gly Phe Met
    210                 215                 220

Asp Glu Ala Asp Arg Ala Leu Arg Asp Ala Asp Trp Ala Ala Ala Gln
225                 230                 235                 240

Thr Ile Asn His Ala Arg Gly Arg Asp Arg Leu Glu Ala Trp Tyr Arg
                245                 250                 255

Ala Gly Leu Thr Ala Gly Gly Thr Gly Glu Asp Trp Thr Gly Trp Tyr
            260                 265                 270

Arg Asp Arg Ile Thr Asn Thr Trp Asp Arg Arg His Asp Asp Ile Tyr
        275                 280                 285

Gly Ala Lys Leu Ile Ala Ser Asp Arg Glu Leu Ala Arg Leu Asp Asp
    290                 295                 300

Gly Pro Asn Ala Thr Leu Asp Pro Ser Pro Ala Ala Ala Gly Gly Trp
305                 310                 315                 320

Val Arg Ile Pro Val Gln Ala Leu Pro Asp Tyr Trp His Cys Gly Thr
                325                 330                 335

Ala Glu Leu Leu Pro Thr Val Pro Thr Arg Pro Val Arg Ala Cys Pro
            340                 345                 350

Pro Pro His Pro Trp Lys Gln Ala Ser Gln Met
        355                 360

<210> SEQ ID NO 24
<211> LENGTH: 216
<212> TYPE: PRT
<213> ORGANISM: Mycobacterium intracellulare

<400> SEQUENCE: 24

Met Thr Pro Pro Arg Val Thr Ser Phe Val Asn Gln Lys Gly Gly Val
1               5                   10                  15

Gly Lys Ser Thr Leu Ala Val Asn Val Ala Ala Glu Lys Ala Arg Arg
            20                  25                  30

Gly Arg Arg Val Leu Leu Leu Asp Ala Asp Gln Gln Gly Thr Ala Leu
        35                  40                  45

Asp Trp Gln Ala Gln Arg Gly Arg Leu Glu His Pro Pro Leu Met Ser
    50                  55                  60

Val Val Gly Phe Pro Arg Asp Thr Ile His Arg Glu Ile Gly Gln Leu
65                  70                  75                  80

Gly Glu Gly Tyr Asp Asp Ile Ile Ile Asp Ala Pro Gly Arg Val Glu
                85                  90                  95

Ala Val Ala Arg Ala Val Ile Met Ala Ser Asp Val Val Val Ile Pro
            100                 105                 110
```

```
Val Gln Pro Ser Ala Tyr Asp Ile Trp Ala Ser Ala Asp Val Leu Thr
        115                 120                 125

Leu Leu Glu Gln Ser Gln Ile Tyr Lys Pro Val Ile Ala Val Trp Val
    130                 135                 140

Ile Asn Arg Arg Ile Val Asn Thr Lys Ile Ala Arg Asp Val Lys Gln
145                 150                 155                 160

Gln Leu Ser Glu Tyr Gly Pro Arg Leu Leu Glu Ala Asn Val Ala Asn
                165                 170                 175

Arg Val Ile Tyr Ser Glu Ala Asn Gly Leu Gly Leu Ala Val Tyr Glu
            180                 185                 190

Ser Asp Pro Gly Gly Val Ala Asp Asp Glu Ile Arg Ala Val Thr Thr
        195                 200                 205

Glu Leu Glu Ala Ile Asn His Gly
    210                 215

<210> SEQ ID NO 25
<211> LENGTH: 628
<212> TYPE: PRT
<213> ORGANISM: Mycobacterium intracellulare

<400> SEQUENCE: 25

Met Asp Glu His Leu Ile Ile Thr Gly Gly Arg Thr Tyr Arg Ile Pro
1               5                   10                  15

Ala Gly Asp Asn Glu Asp Met Asp Ala Leu Leu Ala Trp Trp Val Glu
            20                  25                  30

Ser Arg Gly Glu Pro Ala Ser Val Ala Ala Leu Ser Arg Gln Gln Val
        35                  40                  45

Phe Ala Arg Ile Arg Arg Ala Ala Ile Pro Ala Gly Phe Pro Glu Pro
    50                  55                  60

Asp Val Val Ile Gly Asp Thr Asp Arg Asp Ser Gly Gly Phe Val Arg
65                  70                  75                  80

Gly Trp Leu Pro Ala Thr Val Gln Ala Trp Gln Asp Glu Gln Asp Lys
                85                  90                  95

Pro Ala Ala Ser Gly Ala Pro Thr Glu Pro Ala Ala Ala Gly Glu Pro
            100                 105                 110

Val Gly Gln Asp Glu Pro Ala Pro Ala Asp Pro Gly Pro Ala Ala Gly
        115                 120                 125

Asp Asp Glu Asp Val Trp Arg Met Gly Ala Arg Arg Trp Thr Gly Val
    130                 135                 140

Gly Asp Arg Ala Asp Lys Phe Val Arg Ile Leu Thr Ser Arg Gly Ala
145                 150                 155                 160

Leu Thr Pro Ser Gly Val Val Ser Ala Arg Val Pro Leu Asp Ala Ala
                165                 170                 175

Leu Leu Gly Gln Tyr Val Trp Lys His Trp Pro Gln Lys Pro Ala Gln
            180                 185                 190

Thr Pro Gln Leu Trp Val Thr Ala Pro Ala Leu Ala Ala Ala Gly Met
        195                 200                 205

Ser Pro Pro Lys Arg Pro Pro Thr Thr Ser Glu Asp Leu Ser Asp Ala
    210                 215                 220

Val Ala Lys Ala Phe Gly Cys Glu Val Thr Ala Ala Thr Ala Gly Trp
225                 230                 235                 240

Phe Thr Ala Gln Phe Arg Asp Pro Ala Gly Gly Val Glu Ala Arg Arg
                245                 250                 255

Val His Leu Val Leu Leu Pro Phe Arg Trp Leu Asp Pro Ala Ser Gln
            260                 265                 270
```

```
Arg Pro Asn Asp Glu Gly Met Ala Gly Thr Arg Gly Ala Ala Ser Glu
            275                 280                 285

Leu Pro Asp Asp Glu Asp Asn Glu Asp Ala Ala Val Ala Val Leu Gly
        290                 295                 300

Glu Arg Ile Ala Trp Leu Ala Ala Leu Ala Asp Lys Thr Asp Ser His
305                 310                 315                 320

Arg Arg Glu Leu Pro Val Val Pro Ala Ala Arg Pro Ala Thr Val Gly
                325                 330                 335

Ala Ala Leu Leu Asp Val Val Arg Lys Arg Glu Arg Lys Pro His Arg
                340                 345                 350

Leu Glu Ala Phe Pro Val Pro Asp Thr Val Ala Ala Glu Thr Pro Arg
            355                 360                 365

Leu Asp Pro Asp Leu Glu Asn Trp Lys Asn Met Pro His Thr Ala Lys
    370                 375                 380

Gly Asp Ala Val Asp Val Glu Val Asp Gln Arg Ala Ala Phe Leu Ala
385                 390                 395                 400

Ser Thr Gly Gln Val Glu Leu Gly Tyr Gly Arg Pro Val Glu Met Pro
                405                 410                 415

Lys Val Asp Ala Ala Val Phe Ala Asp Lys Pro Pro Phe Gly Leu Trp
                420                 425                 430

Arg Val Thr Thr Pro Pro Ala Ala Ser Leu Asp Gly Leu Ser Arg Arg
            435                 440                 445

Leu Pro Leu Pro His Glu Tyr Met Ala Trp Glu Ala Pro Ala Thr Phe
    450                 455                 460

Trp Ala Thr Thr Arg Ala Val Gln His Leu Leu Ala Pro Val Asp Asp
465                 470                 475                 480

Gly Gly Ala Gly Val Ser Ile Gly Glu Leu Ala Ile Asp Gly Ala Trp
                485                 490                 495

Val Trp Pro Gly His Ala Arg Leu Leu Arg Asn Trp Ala Asp Leu Leu
            500                 505                 510

Arg Asp Arg Leu Ala Ala Leu Ala Asp Gly Asp Gln Phe Gln Thr
            515                 520                 525

Asp Met Leu Lys Asn Ile Tyr Lys Ala Phe Leu Gly Arg Met Ala Gly
    530                 535                 540

Ser Gln His Pro Pro Gly Gln Arg His Tyr Gln Pro Val Trp Val
545                 550                 555                 560

Ala Thr Ile His Ala Asp Thr Arg Trp Arg Ala Met Arg Tyr Ala Thr
                565                 570                 575

Ala Thr Ala Ala Thr His Gly Leu Tyr Pro Ile Ala Ala Arg Asp Ile
                580                 585                 590

Asp Thr Phe Val Tyr Arg Ile Pro Ala Asp Met Asp Pro Ala Val Leu
            595                 600                 605

Ser Glu Glu Ser Thr Ala Asn Gly Lys Tyr Arg Val Lys Lys Val Arg
    610                 615                 620

Thr Gly Asp His
625

<210> SEQ ID NO 26
<211> LENGTH: 107
<212> TYPE: PRT
<213> ORGANISM: Mycobacterium intracellulare
```

<400> SEQUENCE: 26

Met Arg Gly Glu Leu Trp Thr Ala Ser Gly Arg Asp Tyr Ala Gly Lys
1               5                   10                  15

Pro Arg Pro Val Leu Val Val Gln Asp Asp Arg Phe Asp Ala Thr Asp
            20                  25                  30

Ser Val Thr Ile Cys Pro Leu Thr Asn Thr Thr Gly Ala Pro Leu
        35                  40                  45

Leu Arg Ile Pro Val Gln Pro Asn Ala Ser Asn Gly Leu Thr Thr Pro
    50                  55                  60

Ser His Ile Met Ile Asp Lys Ile Thr Thr Val Pro Arg Ser Lys Ile
65                  70                  75                  80

Gly Gln Arg Ile Gly Lys Val Ser Thr Thr Glu Met Leu Gln Leu Glu
                85                  90                  95

Arg Gly Leu Leu Val Phe Leu Gly Met Thr Gly
            100                 105

<210> SEQ ID NO 27
<211> LENGTH: 175
<212> TYPE: PRT
<213> ORGANISM: Mycobacterium intracellulare

<400> SEQUENCE: 27

Met Lys Pro Gln Leu Gln Val Gly His Trp Tyr Leu Val His Val Glu
1               5                   10                  15

Gly Lys His Thr Ser Val Arg Ala Tyr Met Glu Gly Gly Trp Tyr Pro
            20                  25                  30

Arg Asp Pro Trp Pro Thr Lys Ala Leu Cys Glu Met Ser Arg Val Gly
        35                  40                  45

Asn Pro Tyr His Pro Asp Asp Ile Glu Leu Pro Asp Lys Pro Asp Val
    50                  55                  60

Thr Glu Ile Asp Arg Ala Leu Ile Glu Gln His Tyr Pro Ala Ala Lys
65                  70                  75                  80

Thr His Pro Leu Ile Ala Gly Ala Ile Tyr Asn Met Ala Met Gly Leu
                85                  90                  95

Cys Leu Ala Asn Gly Lys Glu Trp Asn Trp Glu Leu Pro Asp Ala Asp
            100                 105                 110

Pro Gln Pro His Ile Asp Ser Leu Val Leu Ala Cys Ser Val Leu Thr
        115                 120                 125

Asp Met Val Gly Pro Asn Gly Val Val Arg Asp Ile Thr Asp Met Glu
    130                 135                 140

Ala Thr Ser Gly Pro Pro Met Gly Trp Phe Arg Pro Arg Lys Trp Pro
145                 150                 155                 160

Ser Glu Ile Ile Pro Gly Ala Val Pro Leu Gly Glu Ile Ala Ala
                165                 170                 175

<210> SEQ ID NO 28
<211> LENGTH: 59
<212> TYPE: PRT
<213> ORGANISM: Mycobacterium intracellulare

<400> SEQUENCE: 28

Met Thr Ser Gly Asp Arg Glu Asp Glu His Arg Arg Gly Ile Thr Leu
1               5                   10                  15

Ala Gln Ile Lys Arg Ala Gly Leu Tyr Thr Arg Pro Thr Ser Pro Gly
            20                  25                  30

Tyr Arg Gln Ala Met Leu Asp Met Val Glu Arg Gly Arg Asp Asp Ala
            35                  40                  45

Gly Arg Ile Gly Asp Thr Glu Arg Pro Gln Arg
    50                  55

<210> SEQ ID NO 29
<211> LENGTH: 68
<212> TYPE: PRT
<213> ORGANISM: Mycobacterium intracellulare

<400> SEQUENCE: 29

Cys Thr Thr Cys Gly Cys Cys Gly Gly Ala Gly Cys Thr Gly Gly
1               5                   10                  15

Gly Gly Cys Cys Ala Gly Gly Cys Thr Gly Gly Cys Cys Thr Gly
                20                  25                  30

Gly Cys Ala Ala Cys Cys Thr Thr Gly Ala Cys Gly Ala Gly Cys
                35                  40                  45

Gly Cys Cys Thr Gly Cys Gly Gly Cys Gly Cys Thr Cys Thr Ala
                50                  55                  60

Thr Gly Thr Gly
65

<210> SEQ ID NO 30
<211> LENGTH: 28
<212> TYPE: DNA
<213> ORGANISM: Mycobacterium intracellulare

<400> SEQUENCE: 30
ttcgtctctg gagtttcgtc tctggagt                                        28

<210> SEQ ID NO 31
<211> LENGTH: 47
<212> TYPE: DNA
<213> ORGANISM: Mycobacterium intracellulare

<400> SEQUENCE: 31
ccccgaaggg acagtcttgc tggactggtc tcacggtagc gcatacc                   47

<210> SEQ ID NO 32
<211> LENGTH: 48
<212> TYPE: DNA
<213> ORGANISM: Mycobacterium celatum

<400> SEQUENCE: 32
ccccgaaggg acgtgtcttg gcggactcgt ctcacggtag cgcatacc                  48

<210> SEQ ID NO 33
<211> LENGTH: 49
<212> TYPE: DNA
<213> ORGANISM: Mycobacterium fortuitum

<400> SEQUENCE: 33
ccctgaaagg gacgtgtctt gctggactcg tctcacggta gcgcacacc                 49

<210> SEQ ID NO 34
<211> LENGTH: 49
<212> TYPE: DNA
<213> ORGANISM: Mycobacterium fortuitum

<400> SEQUENCE: 34
ccctgaaagg gacgtgtctt ggtcgactcg tctcacggta gcgcatgcc                 49

```
<210> SEQ ID NO 35
<211> LENGTH: 48
<212> TYPE: DNA
<213> ORGANISM: Mycobacterium avium

<400> SEQUENCE: 35
ccccgaaggg aactgctttg ctaggcagct ctcacggtag cgcatacc              48

<210> SEQ ID NO 36
<211> LENGTH: 49
<212> TYPE: DNA
<213> ORGANISM: Mycobacterium scrofulaceum

<400> SEQUENCE: 36
ccccgaaggg atcttgactt gacggtcagg tctcacggta gcgcatacc             49

<210> SEQ ID NO 37
<211> LENGTH: 27
<212> TYPE: DNA
<213> ORGANISM: Artificial Sequence
<220> FEATURE:
<223> OTHER INFORMATION: Forward primer for amplifying oriM

<400> SEQUENCE: 37
aagcttaggc gggcaacacg acatctc                                     27

<210> SEQ ID NO 38
<211> LENGTH: 26
<212> TYPE: DNA
<213> ORGANISM: Artificial Sequence
<220> FEATURE:
<223> OTHER INFORMATION: Reverse primer for amplifying oriM

<400> SEQUENCE: 38 ccatggggt tgtgggccga tgtgct                                       26
```